United States Patent
Joshi et al.

(10) Patent No.: US 8,889,705 B2
(45) Date of Patent: Nov. 18, 2014

(54) NOSCAPINE ANALOGS AND THEIR USE IN TREATING CANCERS

(75) Inventors: Harish C. Joshi, Decatur, GA (US); Ritu Aneja, Lilburn, GA (US); Surya N. Vangapandu, Smyrna, GA (US)

(73) Assignee: Emory University, Atlanta, GA (US)

( * ) Notice: Subject to any disclaimer, the term of this patent is extended or adjusted under 35 U.S.C. 154(b) by 144 days.

(21) Appl. No.: 13/488,621

(22) Filed: Jun. 5, 2012

(65) Prior Publication Data

US 2013/0224310 A1 Aug. 29, 2013

Related U.S. Application Data

(63) Continuation of application No. 12/530,158, filed as application No. PCT/US2008/055811 on Mar. 4, 2008, now abandoned.

(60) Provisional application No. 60/904,959, filed on Mar. 5, 2007.

(51) Int. Cl.
| | | |
|---|---|---|
| *A01N 43/42* | (2006.01) | |
| *C07D 491/00* | (2006.01) | |
| *A61K 31/4741* | (2006.01) | |
| *C07D 491/056* | (2006.01) | |
| *A61K 45/06* | (2006.01) | |

(52) U.S. Cl.
CPC ........ *A61K 31/4741* (2013.01); *C07D 491/056* (2013.01); *A61K 45/06* (2013.01)
USPC ............................................ 514/291; 546/90

(58) Field of Classification Search
USPC ............................................ 514/291; 546/90
See application file for complete search history.

(56) References Cited

PUBLICATIONS

Zhou et al. Mol Pharmacol 63:799-807, 2003.*
Aneja, et al. Blood, 2006 107: 2486-2492, Prepublished online Nov. 10, 2005.*
Aneja, R. et al., 2010, "A Novel Microtubule-Modulating Agent Induces Mitochondrially-Driven Caspase-Dependent Apoptosis Via Mitotic Checkpoint Activation in Human Prostate Cancer Cells", Euro J Cancer, 46(9): 1668-1678.
Aneja, R. et al., 2010, "Non-Toxic Melanoma Therapy by a Novel Tublin-Binding Agent", Int J Cancer, 126(1): 256-265.
Karna, P., et al., 2009, Research: EM011 Activates a survivin-dependent apoptotic program in human non-small cell lung cancer cells, Molecular Cancer, 8:93.
Li, S., et al., 2011, Chemoprevention of familial adenomatous polyposis by bromo-noscapine (EM011) in the Apc-min/+ mouse model, Int J Cancer, 000,000-000.

* cited by examiner

*Primary Examiner* — Nizal Chandrakumar
(74) *Attorney, Agent, or Firm* — Emory Patent Group

(57) ABSTRACT

Compounds, pharmaceutical compositions including the compounds, and methods of preparation and use thereof are disclosed. The compounds are noscapine analogs. The compounds and compositions can be used to treat and/or prevent a wide variety of cancers, including drug resistant cancers. While the antitussive plant alkaloid, noscapine, binds tubulin, displays anticancer activity, and has a safe pharmacological profile in humans, structure-function analyzes pointed to a proton at position 9 of the isoquinoline ring that can be modified without compromising tubulin binding activity. Noscapine analogs with various functional moieties at position 9 on the isoquinoline ring kill human cancer cells resistant to other anti-microtubule agents, such as vincas and taxanes.

6 Claims, 10 Drawing Sheets
(6 of 10 Drawing Sheet(s) Filed in Color)

NOSCAPINE ANALOGS AND THEIR USE IN TREATING CANCERS

CROSS REFERENCE TO RELATED APPLICATIONS

This application is a continuation and claims priority to U.S. application Ser. No. 12/530,158 filed Feb. 9, 2010, now abandoned which is a 371 Application of PCT/US2008/055811 filed Mar. 4, 2008, which claims priority to U.S. Provisional Application No. 60/904,959 filed Mar. 3, 2007, which applications are hereby incorporated by this reference in their entireties.

STATEMENT REGARDING FEDERAL FUNDED RESEARCH

This invention was made with government support under Grant 1 RO1CA095317-01A2 awarded by the National Institutes of Health and National Cancer Institute. The government has certain rights in the invention.

FIELD OF THE INVENTION

The present invention relates to noscapine analogs, pharmaceutical compositions incorporating the noscapine analogs, and methods of using the compounds and compositions to treat cancers, including drug resistant cancers.

BACKGROUND OF THE INVENTION

Microtubules are major cytoskeletal structures responsible for maintaining genetic stability during cell division (Sammak and Borisy, 1987; McIntosh, 1994; Desai and Mitchinson, 1997). The dynamics of these polymers is absolutely crucial for this function that can be described as their growth rate at the plus ends, catastrophic shortening, frequency of transition between the two phases, pause between the two phases, their release from the microtubule organizing center and treadmilling (Margolis and Wilson, 1981; Mitchison and Kirschner, 1984; Kirschner and Mitchison, 1986; Margolis and Wilson, 1998; Jordan and Wilson, 2004). Microtubule lattice also serves as tracks for the axonal transport of organelles driven by anteriograde and retrograde molecular motors to generate and maintain axonal integrity (Joshi, 1998; Nogales, 2000). Interference with microtubule dynamics often leads to programmed cell death and thus microtubule-binding drugs are currently used to treat various malignancies in the clinic (Jordan and Wilson, 2004). Although useful, currently used microtubule drugs such as vincas and taxanes are limited due to the emergence of drug resistance. There have been multiple mechanisms for antimicrotubule drug resistance including overexpression of drug-efflux pumps, misexpression of tubulin isotypes, and perhaps mutational lesions in tubulin itself (Ranganathan et al., 1996; Giannakakou et al., 1997; Monzo et al., 1999; Dumontet et al., 2005).

The pharmacological profile of microtubule-binding agents, however, has not been ideal. Most of them need to be infused over long periods of time in the clinic because they are not water-soluble, and can cause hypersensitive reactions due to the vehicle solution (Rowinsky, 1997). Furthermore, normally dividing cells within the healthy tissues such as intestinal crypts, hair follicles, and the bone marrow are also vulnerable to these agents, leading to toxicities (Rowinsky, 1997). In addition, nerve cells dependent on molecular traffic over long distances undergo degenerative changes causing peripheral neuropathies (Pace et al., 1996; Crown and O'Leary, 2000; Theiss and Meller, 2000; Topp et al., 2000).

Noscapine ((S)-6,7-dimethoxy-3-((R)-4-methoxy-6-methyl-5,6,7,8-tetrahydro[1,3]-dioxolo-[4,5-g]isoquinolin-5-yl)isobenzo-furan-1(3H)-one), a safe antitussive agent for over 40 years, binds tubulin, arrests dividing cells in mitosis and induces apoptosis (Ye et al., 1998). It is well-tolerated in humans and has been shown to be non-toxic in healthy volunteers, including pregnant mothers (Dahlstrom et al., 1982; Karlsson et al., 1990; Jensen et al., 1992).

Unlike the other microtubule-targeting drugs, noscapine does not significantly change the microtubule polymer mass even at high concentrations. Instead, it suppresses microtubule dynamics by increasing the time that microtubules spend in an attenuated (pause) state when neither microtubule growth nor shortening is detectable (Landen et al., 2002). Thus, noscapine-induced suppression of microtubule dynamics, even though subtle, is sufficient to interfere with the proper attachment of chromosomes to kinetochore microtubules and to suppress the tension across paired kinetochores (Zhou et al., 2002a). This represents an improvement over the taxanes, the microtubule-bundling agents or overpolymerizers, and vincas, the depolymerizers, that cause toxicities in mitotic and post mitotic neurons at elevated doses. Noscapine thus effectively inhibits the progression of various cancer types both in cultured cells and in animal models with no obvious side effects (Ye et al., 1998; Landen et al., 2002; Zhou et al., 2002b; 2003; Landen et al., 2004). Surprisingly, the apoptosis is much more pronounced in cancer cells compared with normal healthy cells (Landen et al., 2002).

It would be desirable to have compounds, compositions and methods for preventing and/or treating various types of cancer, without significant associated side effects, that provide increased anti-cancer properties to that of noscapine. The present invention provides such compounds, compositions and methods.

SUMMARY OF THE INVENTION

Compounds, pharmaceutical compositions including the compounds, and methods of preparation and use thereof are disclosed. The compounds are noscapine analogs, including functionalization at the 9-position of the isoquinoline ring. The synthesis, characterization and an evaluation of the anti-tumor potential of these analogs of noscapine, including 9-nitro-nos, 9-fluoro-nos, 9-bromo-nos, and 9-iodo-nos, are described.

The noscapine analogues bind tubulin, effectively inhibit cell proliferation of 1A9 (ovarian cancer cells) and its paclitaxel-resistant variant (1A9/PTX22), and human lymphoblastoid cells CEM, and its vinblastine- (CEMNLB100) and teniposide-(CEM/VM-1-5) resistant variants.

Treatment with one or more of these compounds selectively halts cell cycle progression at the G2/M phase in cancer cells without affecting the cell cycle of normal human fibroblast cells. This mitotic catastrophe in cancer cells is then followed by induction of apoptosis. The apoptotic mechanism is associated with activation of the key executioner cysteine protease, caspase-3. Most importantly, These compounds are more potent against cancer cells that have become resistant to currently used drugs, like vinblastine, teniposide and paclitaxel, as compared to their respective sensitive-parent lines.

The pharmaceutical compositions include an effective amount of the compounds described herein, along with a pharmaceutically acceptable carrier or excipient. When employed in effective amounts, the compounds can act as a therapeutic agent to prevent and/or treat a wide variety of cancers, particularly drug resistant cancers, and are believed to be both safe and effective in this role. Representative cancers that can be treated and/or prevented include drug-resistant ovarian cancer, drug resistant T-cell lymphoma, leukemia, non-small cell lung, colon, central nervous system (CNS), melanoma, renal, ovarian, breast and prostate cancer.

The foregoing and other aspects of the present invention are explained in detail in the detailed description and examples set forth below.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIGS. 3A-H are graphs showing the ability of 9-nitro-nos to arrest the cell cycle at the G2/M phase in human cancer cells. FIGS. 3 C-G show an increase in the population of cells with degraded DNA (sub-G1 amount in the far left) in the three-dimensional fluorescence activated cell sorting analysis (FACS) of DNA amounts. FIG. 3 H shows the effect of 9-nitro-nos on the cell cycle profile of normal primary fibroblast cells. Even concentrations as high as 100 μM, did not alter the cell cycle progression profile of normal human cells. All cells were harvested for analysis at the indicated times, stained with propidium iodide and analyzed by flow cytometry (FACS) using the Cell Quest Software. The x-axis shows intensity of PI-fluorescence, which is indicative of the total DNA content of cells in different phases of the cell cycle. The y-axis represents the number of cells in each phase of the cell cycle and the z-axis shows the time points viz. 0, 24, 48 and 72 hours. Results are representative of three experiments performed in triplicate.

In FIG. 5A, the tubulin fluorescence emission spectrum is quenched by 9-F-nos [Control (■), 25 μM (●), 50 μM (▲), 75 μM (▼), and 100 μM (♦)], 9-Cl-nos [Control (♦), 25 μM (▼), 50 μM (▼), 75 μM (●), and 100 μM (■)], 9-Br-nos [Control (■), 25 μM (●), 50 μM (▲), 75 μM (▼), and 100 μM (♦)] and 9-I-nos [Control (■), 25 μM (▼), 50 μM (▲), 75 μM (♦), and 100 μM (○)] in a concentration-dependent manner.

FIG. 5B is a series of double reciprocal plots showing a dissociation constant ($K_d$) of 81±8 for 9-F-nos binding to tubulin, 40±8 μM for 9-Cl-nos, 54±9.1 μM for 9-Br-nos and 22±4 μM for 9-I-nos. Values are mean±SD for four experiments performed in triplicate ($p<0.05$). The graphs shown are a representative of four experiments performed.

FIGS. 8A-G are a series of charts showing that noscapine and its halogenated analogs inhibit cell cycle progression at mitosis followed by the appearance of a characteristic hypodiploid (sub-G1) DNA peak, indicative of apoptosis. FIGS. 8 E and F show similar three-dimensional profiles for MCF-7 cells treated for 72 hours with 5 µM and 10 µM concentration of each compound to evaluate the differences in percent sub-G1 population among the five compounds. FIG. 8 G is a graphical representation of the quantitation of apoptotic index (percent sub-G1 cells) at the three dose regimes (5 µM, 10 µM and 25 µM) at 72 hours for all compounds. Values and error bars shown in the graph represent the means and standard deviations, respectively of three independent experiments performed in triplicate.

DETAILED DESCRIPTION OF THE INVENTION

Figure 1:
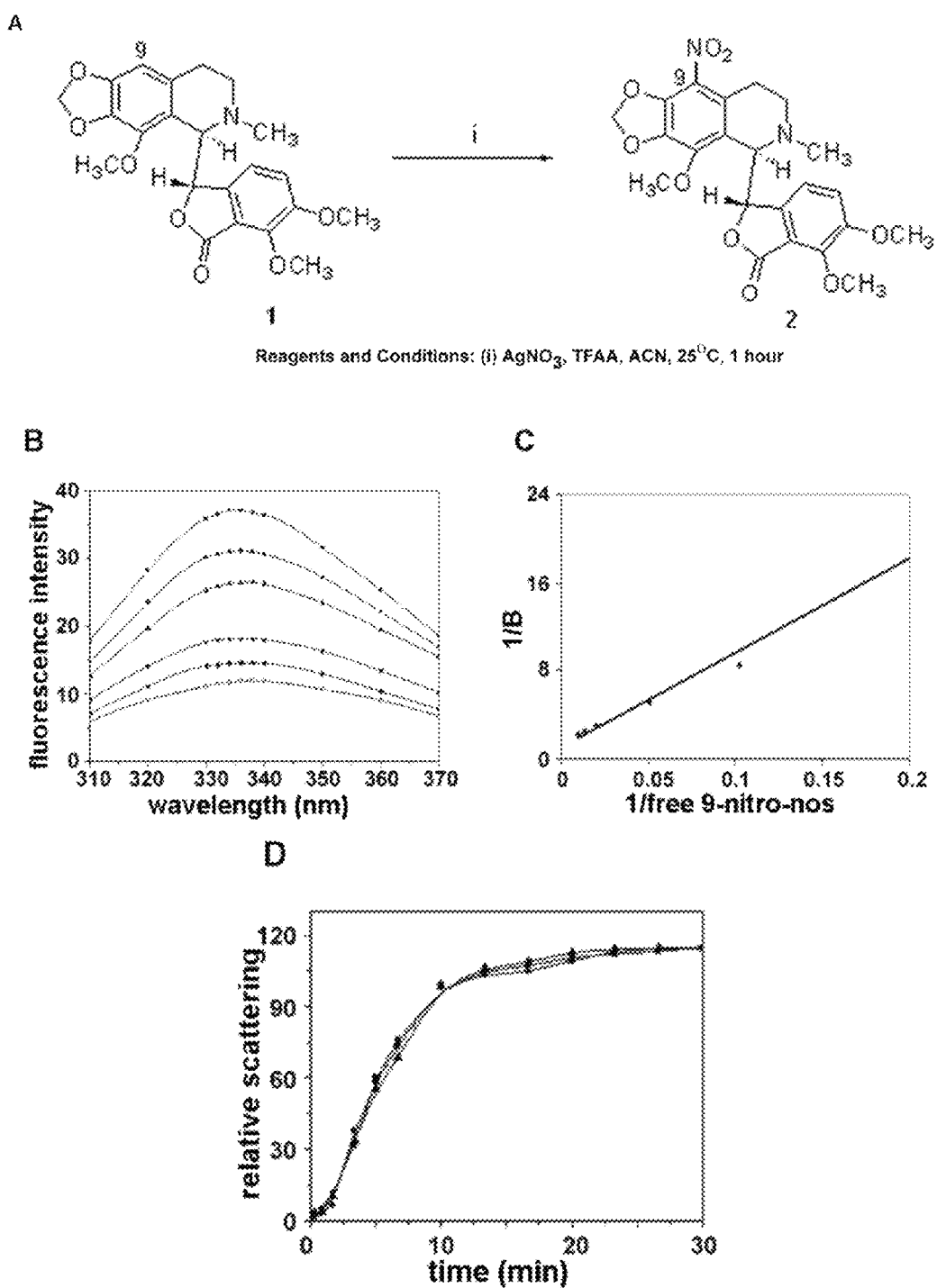
FIG. 1A is a schematic illustration of the synthesis of 9-nitronoscapine from noscapine, using silver nitrate in acetonitrile and TFAA at 25° C.
FIG. 1B is a panel showing the tubulin-binding properties of 9-nitro-nos. Panel B shows the fluorescence quenching spectrum of tubulin for 9-nitro-nos, in fluorescence intensity versus wavelength (nm). Control (■), 10 μM (●), 20 μM (▲), 50 μM (▼), 75 μM (♦), and 100 μM (○) of 9-nitro-nos.
FIG. 1C shows a double reciprocal plot which gives a dissociation constant ($K_d$) of 86±6 μM for 9-nitro-nos binding to tubulin.
FIG. 1D is a plot showing the polymerization rate and steady state polymer mass of tubulin in vitro. The assay was based on the light scattering ability of tubulin polymer, reflected as the absorbance at 550 nm wavelength. An equivalent amount of the solvent DMSO was used as a negative control. Control (■), 25 μM 9-nitro-nos (●), and 100 μM 9-nitro-nos (▲). Results are representative of four independent experiments performed.

Compounds, pharmaceutical compositions including the compounds, and methods of preparation and use thereof are disclosed.

The following definitions will be useful in understanding the metes and bounds of the invention as described herein.

As used herein, "alkyl" refers to straight chain or branched alkyl radicals including $C_1$-$C_8$, preferably $C_1$-$C_5$, such as methyl, ethyl, or isopropyl; "substituted alkyl" refers to alkyl radicals further bearing one or more substituent groups such as hydroxy, alkoxy, aryloxy, mercapto, aryl, heterocyclo, halo, amino, carboxyl, carbamyl, cyano, and the like; "alkenyl" refers to straight chain or branched hydrocarbon radicals including $C_1$-$C_8$, preferably $C_1$-$C_5$ and having at least one carbon-carbon double bond; "substituted alkenyl" refers to alkenyl radicals further bearing one or more substituent groups as defined above; "cycloalkyl" refers to saturated or unsaturated, non-aromatic, cyclic ring-containing radicals containing three to eight carbon atoms, preferably three to six carbon atoms; "substituted cycloalkyl" refers to cycloalkyl radicals further bearing one or more substituent groups as defined above; "aryl" refers to aromatic radicals having six to ten carbon atoms; "substituted aryl" refers to aryl radicals further bearing one or more substituent groups as defined above; "alkylaryl" refers to alkyl-substituted aryl radicals; "substituted alkylaryl" refers to alkylaryl radicals further bearing one or more substituent groups as defined above; "arylalkyl" refers to aryl-substituted alkyl radicals; "substituted arylalkyl" refers to arylalkyl radicals further bearing one or more substituent groups as defined above; "heterocyclyl" refers to saturated or unsaturated cyclic radicals containing one or more heteroatoms (e.g., O, N, S) as part of the ring structure and having two to seven carbon atoms in the ring; "substituted heterocyclyl" refers to heterocyclyl radicals further bearing one or more substituent groups as defined above.

I. Compounds

The compounds are noscapine analogs, prodrugs or metabolites of these compounds, and pharmaceutically acceptable salts thereof. The compounds generally fall within one of the two formulas provided below:

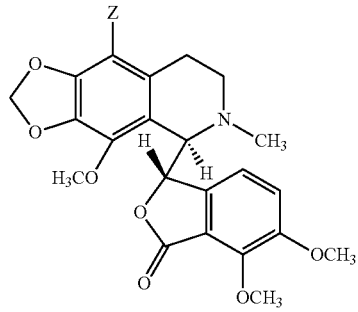

Formula I wherein Z is, individually, selected from the group consisting of alkyl, substituted alkyl, alkenyl, substituted alkenyl, heterocyclyl, substituted heterocyclyl, cycloalkyl, substituted cycloalkyl, aryl, substituted aryl, alkylaryl, substituted alkylaryl, arylalkyl, substituted arylalkyl, —OR', —NR'R", —CF$_3$, —CN, —C$_2$R', —SR', —N$_3$, —C(=O)NR'R", —NR'C(=O) R", —C(=O)R', —C(=O)OR', —OC(=O) R', —O(CR'R")$_r$C(=O)R', —O(CR'R")$_r$NR"C(=O)R', —O(CR'R")$_r$NR"SO$_2$R', —OC(=O)NR'R", —NR'C(=O) OR", —SO$_2$R', —SO$_2$NR'R", and —NR'SO$_2$R", where R' and R" are individually hydrogen, $C_1$-$C_8$ alkyl, cycloalkyl, heterocyclyl, aryl, or arylalkyl, and r is an integer from 1 to 6, wherein the term "substituted" as applied to alkyl, aryl, cycloalkyl and the like refers to the substituents described above, starting with alkyl and ending with —NR'SO$_2$R"; and

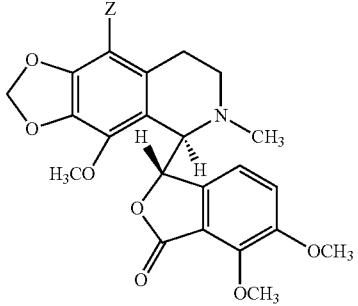

Formula II wherein Z is nitro, bromo, iodo, or fluoro.

The compounds of both formulas can occur in varying degrees of enantiomeric excess.

The compounds can be in a free base form or in a salt form (e.g., as pharmaceutically acceptable salts). Examples of suitable pharmaceutically acceptable salts include inorganic acid addition salts such as sulfate, phosphate, and nitrate; organic acid addition salts such as acetate, galactarate, propionate, succinate, lactate, glycolate, malate, tartrate, citrate, maleate, fumarate, methanesulfonate, p-toluenesulfonate, and ascorbate; salts with an acidic amino acid such as aspartate and glutamate; alkali metal salts such as sodium and potassium; alkaline earth metal salts such as magnesium and calcium; ammonium salt; organic basic salts such as trimethylamine, triethylamine, pyridine, picoline, dicyclohexylamine, and N,N'-dibenzylethylenediamine; and salts with a basic amino acid such as lysine and arginine. The salts can be in some cases hydrates or ethanol solvates. The stoichiometry of the salt will vary with the nature of the components.

Representative compounds include the following:

9-Nitro-Nos ((S)-6,7-dimethoxy-3-((R)-4-methoxy-6-methyl-9-nitro-5,6,7,8-tetrahydro-[1,3]dioxolo[4,5-g]isoquinolin-5-yl)isobenzofuran-1(3H)-one)

9-Iodo-Nos ((S)-6,7-dimethoxy-3-((R)-4-methoxy-6-methyl-9-iodo-5,6,7,8-tetrahydro-[1,3]dioxolo[4,5-g]isoquinolin-5-yl)isobenzofuran-1(3H)-one)

9-Bromo-Nos ((S)-6,7-dimethoxy-3-((R)-4-methoxy-6-methyl-9-bromo-5,6,7,8-tetrahydro-[1,3]dioxolo[4,5-g]isoquinolin-5-yl)isobenzofuran-1(3H)-one) and 9-Fluoro-Nos ((S)-6,7-dimethoxy-3-((R)-4-methoxy-6-methyl-9-fluoro-5,6,7,8-tetrahydro-[1,3]dioxolo[4,5-g]isoquinolin-5-yl)isobenzofuran-1(3H)-one).

II. Methods of Preparing the Compounds

The compounds can be prepared by performing electrophilic aromatic substitution on the isoquinoline ring of noscapine, typically under conditions that do not result in significant hydrolysis of the noscapine framework. The substituents typically are added to the 9-position on the isoquinoline ring, although yields can be optimized and byproducts may be present and need to be removed during a purification step. More optimized syntheses of representative compounds, such as 9-nitro-nos, 9-iodo-nos, 9-bromo-nos, and 9-iodo-nos, are provided in the Examples section.

Briefly, the nitration of the isoquinoline ring in noscapine can be accomplished by using stoichiometric silver nitrate and a slight excess of trifluoroacetic anhydride.

The halogenation of noscapine involved various procedures, which varied depending on the particular halogen, as summarized below in Scheme 1.

Scheme 1
Semi-synthetic derivatives of noscapine.

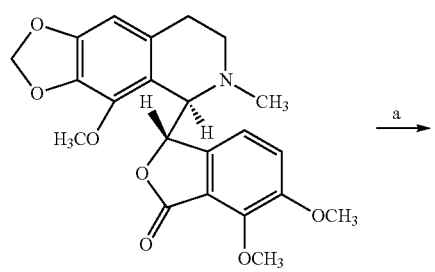

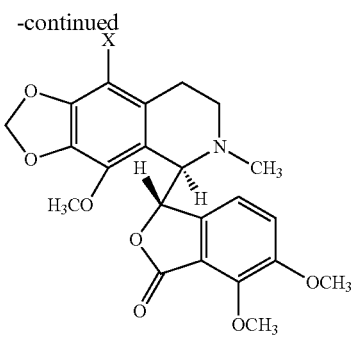

Reagents and reaction conditions - a) compound 2: Br$_2$ — H$_2$O; 48% HBr, 82%; Compound 4: SO$_2$Cl$_2$, CHCl$_3$, 90%; Compound 5: Pyr — ICl, CH$_3$CN, 71%. b) F$_2$, Amberlyst-A, THF, 74%

Noscapine can be brominated at the 9-position by reacting noscapine with concentrated hydrobromic acid. Noscapine can be fluorinated using the fluoride form of Amberlyst-A 26, or by Br/F exchange. Iodination of noscapine typically required low-acid conditions. One successful approach for preparing 9-I-nos involved treating a solution of noscapine in acetonitrile with pyridine-iodine chloride at room temperature for 6 hours followed by raising the temperature to 100° C. for another 6 hours.

Those skilled in the art that incorporation of other substituents onto the 9-position of the isoquinoline ring, and other positions in the noscapine framework, can be readily realized. Such substituents can provide useful properties in and of themselves or serve as a handle for further synthetic elaboration.

A number of other analogs, bearing substituents in the 9 position of the isoquinoline ring, can be synthesized from the corresponding amino compounds, via a 9-diazonium salt intermediate. The diazonium intermediate can be prepared, using known chemistry, by reduction of the 9-nitro compound to the 9-nitro amine compound, followed by reaction with a nitrite salt, typically in the presence of an acid. Examples of other 9-substituted analogs that can be produced from 9-diazonium salt intermediates include, but are not limited to: 9-hydroxy, 9-alkoxy, 9-fluoro, 9-chloro, 9-iodo, 9-cyano, and 9-mercapto. These compounds can be synthesized using the general techniques set forth in Zwart et al., supra. For example, the 9-hydroxy-noscapine analogue can be prepared from the reaction of the corresponding 9-diazonium salt intermediate with water. Likewise, 9-alkoxy noscapine analogues can be made from the reaction of the 9-diazonium salt with alcohols. Appropriate 9-diazonium salts can be used to synthesize cyano or halo compounds, as will be known to those skilled in the art. 9-Mercapto substitutions can be obtained using techniques described in Hoffman et al., *J. Med. Chem.* 36: 953 (1993). The 9-mercaptan so generated can, in turn, be converted to a 9-alkylthio substitutuent by reaction with sodium hydride and an appropriate alkyl bromide. Subsequent oxidation would then provide a sulfone. 9-Acylamido analogs of the aforementioned compounds can be prepared by reaction of the corresponding 9-amino compounds with an appropriate acid anhydride or acid chloride using techniques known to those skilled in the art of organic synthesis.

9-Hydroxy-substituted analogs of the aforementioned compounds can be used to prepare corresponding 9-alkanoyloxy-substituted compounds by reaction with the appropriate acid, acid chloride, or acid anhydride. Likewise, the 9-hydroxy compounds are precursors of both the 9-aryloxy and 9-heteroaryloxy via nucleophilic aromatic substitution at electron deficient aromatic rings. Such chemistry is well known to those skilled in the art of organic synthesis. Ether derivatives can also be prepared from the 9-hydroxy compounds by alkylation with alkyl halides and a suitable base or via Mitsunobu chemistry, in which a trialkyl- or triarylphosphine and diethyl azodicarboxylate are typically used. See Hughes, *Org. React.* (N.Y.) 42: 335 (1992) and Hughes, *Org. Prep. Proced. Int.* 28: 127 (1996) for typical Mitsunobu conditions.

9-Cyano-substituted analogs of the aforementioned compounds can be hydrolyzed to afford the corresponding 9-carboxamido-substituted compounds. Further hydrolysis results in formation of the corresponding 9-carboxylic acid-substituted analogs. Reduction of the 9-cyano-substituted analogs with lithium aluminum hydride yields the corresponding 9-aminomethyl analogs. 9-Acyl-substituted analogs can be prepared from corresponding 9-carboxylic acid-substituted analogs by reaction with an appropriate alkyllithium using techniques known to those skilled in the art of organic synthesis.

9-Carboxylic acid-substituted analogs of the aforementioned compounds can be converted to the corresponding esters by reaction with an appropriate alcohol and acid catalyst. Compounds with an ester group at the 9-pyridyl position can be reduced with sodium borohydride or lithium aluminum hydride to produce the corresponding 9-hydroxymethyl-substituted analogs. These analogs in turn can be converted to compounds bearing an ether moiety at the 9-pyridyl position by reaction with sodium hydride and an appropriate alkyl halide, using conventional techniques. Alternatively, the 9-hydroxymethyl-substituted analogs can be reacted with tosyl chloride to provide the corresponding 9-tosyloxymethyl analogs. The 9-carboxylic acid-substituted analogs can also be converted to the corresponding 9-alkylaminoacyl analogs by sequential treatment with thionyl chloride and an appropriate alkylamine. Certain of these amides are known to readily undergo nucleophilic acyl substitution to produce ketones.

9-Hydroxy-substituted analogs can be used to prepare 9-N-alkyl- or 9-N-arylcarbamoyloxy-substituted compounds by reaction with N-alkyl- or N-arylisocyanates. 9-Amino-substituted analogs can be used to prepare 9-alkoxycarboxamido-substituted compounds and 9-urea derivatives by reaction with alkyl chloroformate esters and N-alkyl- or N-arylisocyanates, respectively, using techniques known to those skilled in the art of organic synthesis.

III. Pharmaceutical Compositions

The compounds described herein can be incorporated into pharmaceutical compositions and used to prevent a condition or disorder in a subject susceptible to such a condition or disorder, and/or to treat a subject suffering from the condition or disorder. The pharmaceutical compositions described herein include one or more of the noscapine analogues described herein, and/or pharmaceutically acceptable salts thereof. Optically active compounds can be employed as racemic mixtures, as pure enantiomers, or as compounds of varying enantiomeric purity.

The manner in which the compounds are administered can vary. The compositions are preferably administered orally (e.g., in liquid form within a solvent such as an aqueous or non-aqueous liquid, or within a solid carrier). Preferred compositions for oral administration include pills, tablets, capsules, caplets, syrups, and solutions, including hard gelatin capsules and time-release capsules. Compositions may be formulated in unit dose form, or in multiple or subunit doses. Preferred compositions are in liquid or semisolid form. Compositions including a liquid pharmaceutically inert carrier such as water or other pharmaceutically compatible liquids or semisolids may be used. The use of such liquids and semisolids is well known to those of skill in the art.

The compositions can also be administered via injection, i.e., intraveneously, intramuscularly, subcutaneously, intraperitoneally, intraarterially, intrathecally; and intracerebroventricularly. Intravenous administration is a preferred method of injection. Suitable carriers for injection are well known to those of skill in the art, and include 5% dextrose solutions, saline, and phosphate buffered saline. The compounds can also be administered as an infusion or injection (e.g., as a suspension or as an emulsion in a pharmaceutically acceptable liquid or mixture of liquids).

The formulations may also be administered using other means, for example, rectal administration. Formulations useful for rectal administration, such as suppositories, are well known to those of skill in the art. The compounds can also be administered by inhalation (e.g., in the form of an aerosol either nasally or using delivery articles of the type set forth in U.S. Pat. No. 4,922,901 to Brooks et al., the disclosure of which is incorporated herein in its entirety); topically (e.g., in lotion form); or transdermally (e.g., using a transdermal patch, using technology that is commercially available from Novartis and Alza Corporation). Although it is possible to administer the compounds in the form of a bulk active chemical, it is preferred to present each compound in the form of a pharmaceutical composition or formulation for efficient and effective administration.

Exemplary methods for administering such compounds will be apparent to the skilled artisan. The usefulness of these formulations may depend on the particular composition used and the particular subject receiving the treatment. These formulations may contain a liquid carrier that may be oily, aqueous, emulsified or contain certain solvents suitable to the mode of administration.

The compositions can be administered intermittently or at a gradual, continuous, constant or controlled rate to a warm-blooded animal (e.g., a mammal such as a mouse, rat, cat, rabbit, dog, pig, cow, or monkey), but advantageously are administered to a human being. In addition, the time of day and the number of times per day that the pharmaceutical formulation is administered can vary.

Preferably, the compositions are administered such that active ingredients interact with regions where cancer cells are located. The compounds described herein are very potent at treating these cancers.

In certain circumstances, the compounds described herein can be employed as part of a pharmaceutical composition with other compounds intended to prevent or treat a particular cancer, i.e., combination therapy. In addition to effective amounts of the compounds described herein, the pharmaceutical compositions can also include various other components as additives or adjuncts.

Combination Therapy

The combination therapy may be administered as (a) a single pharmaceutical composition which comprises a noscapine analogue as described herein, at least one additional pharmaceutical agent described herein, and a pharmaceutically acceptable excipient, diluent, or carrier; or (b) two separate pharmaceutical compositions comprising (i) a first composition comprising a noscapine analogue as described herein and a pharmaceutically acceptable excipient, diluent, or carrier, and (ii) a second composition comprising at least one additional pharmaceutical agent described herein and a pharmaceutically acceptable excipient, diluent, or carrier. The pharmaceutical compositions can be administered simultaneously or sequentially and in any order.

In use in treating or preventing cancer, the noscapine analogues described herein can be administered together with at least one other chemotherapeutic agent as part of a unitary pharmaceutical composition. Alternatively, the noscapine analogues can be administered apart from the other anticancer chemotherapeutic agent. In this embodiment, the noscapine analogues and the at least one other anticancer chemotherapeutic agent are administered substantially simultaneously, i.e. the compounds are administered at the same time or one after the other, so long as the compounds reach therapeutic levels for a period of time in the blood.

Combination therapy involves administering a noscapine analogue, as described herein, or a pharmaceutically acceptable salt or prodrug of a compound described herein, in combination with at least one anti-cancer chemotherapeutic agent, ideally one which functions by a different mechanism (i.e., VEGF inhibitors, alkylating agents, and the like).

Examples of known anticancer agents which can be used for combination therapy include, but are not limited to alkylating agents, such as busulfan, cis-platin, mitomycin C, and carboplatin; antimitotic agents, such as colchicine, vinblastine, paclitaxel, and docetaxel; topo I inhibitors, such as camptothecin and topotecan; topo II inhibitors, such as doxorubicin and etoposide; RNA/DNA antimetabolites, such as 5-azacytidine, 5-fluorouracil and methotrexate; DNA antimetabolites, such as 5-fluoro-2'-deoxy-uridine, ara-C, hydroxyurea and thioguanine; and antibodies, such as Herceptin® and Rituxan®. Other known anti-cancer agents, which can be used for combination therapy, include arsenic trioxide, gamcitabine, melphalan, chlorambucil, cyclophosphamide, ifosfamide, vincristine, mitoguazone, epirubicin, aclarubicin, bleomycin, mitoxantrone, elliptinium, fludarabine, octreotide, retinoic acid, tamoxifen and alanosine. Other classes of anticancer compounds that can be used in combination with the noscapine analogues are described below.

The noscapine analogues can be combined with alpha-1-adrenoceptor antagonists, such as doxazosin, terazosin, and tamsulosin., which can inhibit the growth of prostate cancer cell via induction of apoptosis (Kyprianou, N., et al., Cancer Res 60:4550 4555, (2000)).

Sigma-2 receptors are expressed in high densities in a variety of tumor cell types (Vilner, B. J., et al., Cancer Res. 55: 408 413 (1995)) and sigma-2 receptor agonists, such as CB-64D, CB-184 and haloperidol, activate a novel apoptotic pathway and potentiate antineoplastic drugs in breast tumor cell lines. (Kyprianou, N., et al., Cancer Res. 62:313 322 (2002)). Accordingly, the noscapine analogues can be combined with at least one known sigma-2 receptor agonists, or a pharmaceutically acceptable salt of said agent.

The noscapine analogues can be combined with lovastatin, a HMG-CoA reductase inhibitor, and butyrate, an inducer of apoptosis in the Lewis lung carcinoma model in mice, can potentiate antitumor effects (Giermasz, A., et al., Int. J. Cancer 97:746 750 (2002)). Examples of known HMG-CoA reductase inhibitors, which can be used for combination therapy include, but are not limited to, lovastatin, simvastatin, pravastatin, fluvastatin, atorvastatin and cerivastatin, and pharmaceutically acceptable salts thereof.

Certain HIV protease inhibitors, such as indinavir or saquinavir, have potent anti-angiogenic activities and promote regression of Kaposi sarcoma (Sgadari, C., et al., Nat. Med. 8:225 232 (2002)). Accordingly, the noscapine analogues can be combined with HIV protease inhibitors, or a pharmaceutically acceptable salt of said agent. Representative HIV protease inhibitors include, but are not limited to, amprenavir, abacavir, CGP-73547, CGP-61755, DMP-450, indinavir, nelfinavir, tipranavir, ritonavir, saquinavir, ABT-378, AG 1776, and BMS-232,632.

Synthetic retinoids, such as fenretinide (N-(4-hydroxyphenyl)retinamide, 4HPR), can have good activity in combination with other chemotherapeutic agents, such as cisplatin, etoposide or paclitaxel in small-cell lung cancer cell lines (Kalemkerian, G. P., et al., Cancer Chemother. Pharmacol. 43:145 150 (1999)). 4HPR also was reported to have good activity in combination with gamma-radiation on bladder cancer cell lines (Zou, C., et al., Int. J. Oncol. 13:1037 1041 (1998)). Representative retinoids and synthetic retinoids include, but are not limited to, bexarotene, tretinoin, 13-cis-retinoic acid, 9-cis-retinoic acid, .alpha.-difluoromethylornithine, ILX23-7553, fenretinide, and N-4-carboxyphenyl retinamide.

Proteasome inhibitors, such as lactacystin, exert anti-tumor activity in vivo and in tumor cells in vitro, including those resistant to conventional chemotherapeutic agents. By inhibiting NF-kappaB transcriptional activity, proteasome inhibitors may also prevent angiogenesis and metastasis in vivo and further increase the sensitivity of cancer cells to apoptosis (Almond, J. B., et al., Leukemia 16:433 443 (2002)). Representative proteasome inhibitors include, but are not limited to, lactacystin, MG-132, and PS-341.

Tyrosine kinase inhibitors, such as STI571 (Imatinib mesilate, Gleevec®), have potent synergetic effects in combination with other anti-leukemic agents, such as etoposide (Liu, W. M., et al. Br. J. Cancer 86:1472 1478 (2002)). Representative tyrosine kinase inhibitors include, but are not limited to, Gleevec®, ZD1839 (Iressa®), SH268, genistein, CEP2563, SU6668, SU11248, and EMD121974.

Prenyl-protein transferase inhibitors, such as farnesyl protein transferase inhibitor R115777, possess antitumor activity against human breast cancer (Kelland, L. R., et. al., Clin. Cancer Res. 7:3544 3550 (2001)). Synergy of the protein farnesyltransferase inhibitor SCH66336 and cisplatin in human cancer cell lines also has been reported (Adjei, A. A., et al., Clin. Cancer. Res. 7:1438 1445 (2001)). Prenyl-protein transferase inhibitors, including farnesyl protein transferase inhibitor, inhibitors of geranylgeranyl-protein transferase type I (GGPTase-I) and geranylgeranyl-protein transferase type-II, or a pharmaceutically acceptable salt of said agent, can be used in combination with the noscapine analogues described herein. Examples of known prenylprotein transferase inhibitors include, but are not limited to, R115777, SCH66336, L-778,123, BAL9611 and TAN-1813.

Cyclin-dependent kinase (CDK) inhibitors, such as flavopiridol, have potent, often synergetic, effects in combination with other anticancer agents, such as CPT-11, a DNA topoisomerase I inhibitor in human colon cancer cells (Motwani, M., et al., Clin. Cancer Res. 7:4209 4219, (2001)). Representative cyclin-dependent kinase inhibitors include, but are not limited to, flavopiridol, UCN-01, roscovitine and olomoucine.

Certain COX-2 inhibitors are known to block angiogenesis, suppress solid tumor metastases, and slow the growth of implanted gastrointestinal cancer cells (Blanke, C. D., Oncology (Huntingt) 16(No. 4 Suppl. 3):17 21 (2002)). Representative COX-2 inhibitors include, but are not limited to, celecoxib, valecoxib, and rofecoxib.

Any of the above-mentioned compounds can be used in combination therapy with the noscapine analogues. Further, the noscapine analogues can be targeted to a tumor site by conjugation with therapeutically useful antibodies, such as Herceptin® or Rituxan®, growth factors, such as DGF, NGF;

cytokines, such as IL-2, IL-4, or any molecule that binds to the cell surface. The antibodies and other molecules will deliver a compound described herein to its targets and make it an effective anticancer agent. The bioconjugates can also enhance the anticancer effect of therapeutically useful antibodies, such as Herceptin® or Rituxan®.

The compounds can also be used in conjunction with surgical tumor removal, by administering the compounds before and/or after surgery, and in conjunction with radiation therapy, by administering the compounds before, during, and/or after radiation therapy.

The appropriate dose of the compound is that amount effective to prevent occurrence of the symptoms of the disorder or to treat some symptoms of the disorder from which the patient suffers. By "effective amount", "therapeutic amount" or "effective dose" is meant that amount sufficient to elicit the desired pharmacological or therapeutic effects, thus resulting in effective prevention or treatment of the disorder.

When treating cancers, an effective amount of the noscapine analogue is an amount sufficient to suppress the growth of the tumor(s), and, ideally, is a sufficient amount to shrink the tumor, and, more ideally, to destroy the tumor. Cancer can be prevented, either initially, or from re-occurring, by administering the compounds described herein in a prophylactic manner. Preferably, the effective amount is sufficient to obtain the desired result, but insufficient to cause appreciable side effects.

The effective dose can vary, depending upon factors such as the condition of the patient, the severity of the cancer, and the manner in which the pharmaceutical composition is administered. The effective dose of compounds will of course differ from patient to patient, but in general includes amounts starting where desired therapeutic effects occur but below the amount where significant side effects are observed.

The compounds, when employed in effective amounts in accordance with the method described herein, are selective to certain cancer cells, but do not significantly affect normal cells.

For human patients, the effective dose of typical compounds generally requires administering the compound in an amount of at least about 1, often at least about 10, and frequently at least about 25 µg/24 hr/patient. The effective dose generally does not exceed about 500, often does not exceed about 400, and frequently does not exceed about 300 µg/24 hr/patient. In addition, administration of the effective dose is such that the concentration of the compound within the plasma of the patient normally does not exceed 500 ng/mL and frequently does not exceed 100 ng/mL.

IV. Methods of Using the Compounds and/or Pharmaceutical Compositions

The compounds can be used to treat cancers, including blood-borne and solid tumors. Representative cancers include drug-resistant ovarian cancer, drug resistant T-cell lymphoma, leukemia, non-small cell lung, colon, central nervous system (CNS), melanoma, renal, ovarian, breast and prostate cancer.

The compounds can also be used as adjunct therapy in combination with existing therapies in the management of the aforementioned types of cancers. In such situations, it is preferably to administer the active ingredients to in a manner that optimizes effects upon cancer cells, including drug resistant cancer cells, while minimizing effects upon normal cell types. While this is primarily accomplished by virtue of the behavior of the compounds themselves, this can also be accomplished by targeted drug delivery and/or by adjusting the dosage such that a desired effect is obtained without meeting the threshold dosage required to achieve significant side effects.

The following examples are provided to illustrate the present invention, and should not be construed as limiting thereof. In these examples, all parts and percentages are by weight, unless otherwise noted. Reaction yields are reported in mole percentages.

EXAMPLES

The following examples are provided to illustrate the present invention and should not be construed as limiting the scope thereof. In these examples, all parts and percentages are by weight, unless otherwise noted. Reaction yields are reported in mole percentage.

Chemistry: $^1$H NMR and $^{13}$C NMR spectra were measured by 400 NMR spectrometer in a CDCl$_3$ solution and analyzed by NOVA. Proton NMR spectra were recorded at 400 MHz and were referenced with residual chloroform (7.27 ppm). Carbon NMR spectra were recorded at 100 MHz and were referenced with 77.27 ppm resonance of residual chloroform. Abbreviations for signal coupling are as follows: s, singlet; d, doublet; t, triplet; q, quartet; m, multiplet. Infrared spectra were recorded on sodium chloride discs on Mattson Genesis II FT-IR. High resolution mass spectra were collected on Thermo Finnigan LTQ-FT Hybrid mass spectrophotometer using 3-nitrobenzyl alcohol or with addition of LiI as a matrix. Melting points were determined using a Thomas-Hoover melting point apparatus and were uncorrected. All reactions were conducted with oven-dried (125° C.) reaction vessels in dry argon. All common reagents and solvents were obtained from Aldrich and were dried using 4 Å molecular sieves. The reactions were monitored by thin layer chromatography (TLC) using silica gel 60 F254 (Merck) on precoated aluminum sheets. Flash chromatography was carried out on standard grade silica gel (230-400 mesh).

Example 1

Preparation of 9-Nitro-Nos ((S)-6,7-dimethoxy-3-((R)-4-methoxy-6-methyl-9-nitro-5,6,7,8-tetrahydro-[1,3]dioxolo[4,5-g]isoquinolin-5-yl)isobenzofuran-1 (3H)-one)

To a solution of noscapine (4.134 g, 10 mmol) in acetonitrile (50 ml), silver nitrate (1.70 g, 10 mmol) and trifluoroacetic anhydride (5 ml, 35 mmol) were added. After one hour of reaction time, the reaction progress was monitored using thin layer chromatography (10% methanol in chloroform) and the reaction mixture was poured into 50 ml of water and extracted with chloroform (3×50 ml). The organic layer was washed with brine, dried over anhydrous MgSO$_4$ and the solvent was evaporated in vacuo. The desired product, (S)-6,7-dimethoxy-3-((R)-4-methoxy-6-methyl-9-nitro-5,6,7,8-tetrahydro-[1,3]dioxolo[4,5-g]isoquinolin-5-yl)isobenzofuran-1 (3H)-one (9-nitro-nos) was obtained as yellow crystalline powder by flash chromatography (silica gel, 230-400 mesh) with 10% methanol in chloroform as an eluent. mp 178.2-178.4° C.; IR: 1529, 1362 cm-1; $^1$H NMR (CDCl$_3$, 400 MHz): δ 7.27 (d, 1H, J=8.0 Hz), 7.08 (d, 1H, J=8.0 Hz), 6.02 (s, 2H), 5.91 (d, 1H, J=4.1 Hz), 4.42 (d, 1H, J=4.1 Hz), 4.09 (s, 3H), 3.89 (s, 3H), 3.83 (s, 3H), 2.74-2.64 (m, 2H), 2.61-2.56 (m, 2H), 2.52 (s, 3H); $^{13}$C NMR (CDCl$_3$, 100 MHz): δ 169.7, 157.2, 151.6, 147.5, 142.3, 140.5, 135.0, 134.2, 123.2, 120.8, 119.9, 119.4, 114.1, 100.8, 87.6, 63.7, 56.8, 56.4, 56.1, 51.4, 39.2, 27.0; HRMS (ESI): m/z Calcd. for $C_{22}H_{23}N_2O_9$ (M+1), 459.4821. Found, 459.4755 (M+1).

HPLC Purity and Peak Attributions:

The HPLC purity was determined following two different methods using varied solvent systems.

Method 1: Ultimate Plus, LC Packings, Dionex, C18 column (pep Map 100, 3 μm, 100 Å particle size, ID: 1000 μm, length: 15 cm) with solvent systems A (0.1% formic acid in water) and B (acetonitrile), gradient, 25 min run at a flow of 40 μL/min. Retention time for 9-nitro-nos is 19.30 min. HPLC purity was 96%. Method 2: Ultimate Plus, LC Packings, Dionex, C18 column (pep Map 100, 3 μm, 100 Å particle size, ID: 1000 μm, length: 15 cm) with solvent systems A (0.1% formic acid in water) and B (methanol), gradient, 25 min run at a flow of 40 μL/min. Retention time for 9-nitro-nos is 19.86 min. HPLC purity was 97%.

Discussion of Other Synthetic Approaches

The nitration reaction is a well-studied electrophilic substitution reaction in organic chemistry. Although, fuming nitric acid or 50% nitric acid in glacial acetic acid are extensively used for obtaining the nitrated product, the harsh oxidizing conditions of these reagents did not allow us to use these reagents for the nitration of noscapine. The lead compound, noscapine comprises of isoquinoline and benzofuranone ring systems joined by a labile C—C chiral bond and both these ring systems contain several vulnerable methoxy groups. Thus, achieving selective nitration at C-9 position without disruption and cleavage of these labile groups and C—C bonds was challenging. Treatment of noscapine with other nitrating agents like acetyl nitrate or benzoyl nitrate also resulted in epimerization or diastereoisomers (Lee, 2002). Next, inorganic nitrate salts like ammonium nitrate or silver nitrate were used in the presence of acidic media to achieve aromatic nitration (Crivello, 1981). After carefully titrating several conditions and reagents, the nitration of noscapine using trifluoroacetic anhydride (TFAA) was successfully accomplished. TFAA represents another commonly employed reagent and its extensive use is associated with its ability to generate a mixed anhydride, trifluoroacetyl nitrate that is a reactive nitrating agent (Crivello, 1981). Other reagents such as ammonium nitrate, sodium nitrate or silver nitrate in chloroform were also tried, but those provided low quantitative yields and had longer reaction times. Increased reaction rate and yields were obtained using a lower dielectric constant solvent, acetonitrile. The reaction was slightly exothermic and completed in one hour. The product remained in solution while the inorganic salt of trifluoroacetic acid precipitated and was removed by filtration.

Thus, (S)-6,7-dimethoxy-3-((R)-4-methoxy-6-methyl-9-nitro-5,6,7,8-tetrahydro-[1,3]dioxolo[4,5-g]iso-quinolin-5-yl)isobenzofuran-1 (3H)-one (9-nitro-nos) was prepared by the aromatic nitration of (S)-6,7-dimethoxy-3-((R)-4-methoxy-6-methyl-5,6,7,8-tetrahydro-[1,3]dioxolo[4,5-g]iso-quinolin-5-yl)isobenzo-furan-1 (3H)-one (noscapine) using silver nitrate in acetonitrile and TFAA at 25° C. (FIG. 1A). This method resulted in controlling the chemoselectivity of the reaction, in that aromatic substitution occurred at C-9 position of ring A of the isoquinoline nucleus. Absence of C-9 aromatic proton at δ 6.52-ppm in the $^1H$ NMR spectrum of the product confirmed the nitration at C-9 position. Furthermore, $^{13}C$ NMR and HRMS data confirmed the structure of the compound.

Example 2

Evaluation of the Tumulin Binding Properties of 9-Nitro-Nos

Cell Lines and Chemicals:

Cell culture reagents were obtained from Mediatech, Cellgro. CEM, a human lymphoblastoid line, and its drug-resistant variants-CEMNLB100 and CEM/VM-1-5, were provided by Dr. William T. Beck (Cancer Center, University of Illinois at Chicago). CEM-VLB100, a multi-drug resistant line selected against vinblastine is derived from the human lymphoblastoid line, CEM and expresses high levels of 170-kd P-glycoprotein (Beck and Cirtain, 1982). CEM/VM-1-5, resistant to the epipodophyllotoxin, teniposide (VM-26), expresses a much higher amount of MRP protein than CEM cells (Morgan et al., 2000). The 1A9 cell line is a clone of the human ovarian carcinoma cell line, A2780. The paclitaxel-resistant cell line, 1A9/PTX22, was isolated as an individual clone in a single-step selection, by exposing 1A9 cells to 5 ng/ml paclitaxel in the presence of 5 μg/ml verapamil, a P-glycoprotein antagonist (Giannakakou et al., 1997). All cells were grown in RPMI-1640 medium (Mediatech, Cellgro) supplemented with 10% fetal bovine serum (Invitrogen, Carlsbad, Calif.) and 1% penicillin/streptomycin (Mediatech, Cellgro). Paclitaxel-resistant 1A9/PTX22 cell line was maintained in 15 ng/ml paclitaxel and 5 □g/ml verapamil continuously, but was cultured in drug-free medium for 7 days prior to experiment. Human fibroblast primary cultures were obtained from the Dermatology Department of the Emory Hospital, Atlanta. They were maintained in Dulbecco's Modification of Eagle's Medium 1× (DMEM) with 4.5 g/L glucose and L-glutamine (Mediatech, Cellgro) supplemented with 10% fetal bovine serum and 1% penicillin/streptomycin. Mammalian brain microtubule proteins were isolated by two cycles of polymerization and depolymerization and tubulin was separated from the microtubule binding proteins by phosphocellulose chromatography as described previously (Panda et al., 2000; Joshi and Zhou, 2001). The tubulin solution was stored at −80° C. until use.

Tubulin Binding Assay:

Fluorescence titration for determining the tubulin binding parameters was performed as described previously (Gupta and Panda, 2002). In brief, 9-nitro-nos (0-100 μM) was incubated with 2 μM tubulin in 25 mM PIPES, pH 6.8, 3 mM $MgSO_4$ and 1 mM EGTA for 45 min at 37° C. The relative intrinsic fluorescence intensity of tubulin was then monitored in a JASCO FP-6500 spectrofluorometer (JASCO, Tokyo, Japan) using a cuvette of 0.3-cm path length, and the excitation wavelength was 295 nm. The fluorescence emission intensity of 9-nitro-nos at this excitation wavelength was negligible. A 0.3-cm path-length cuvette was used to minimize the inner filter effects caused by the absorbance of 9-nitro-nos at higher concentration ranges. In addition, the inner filter effects were corrected using a formula Fcorrected=Fobserved·antilog [(Aex+Aem)/2], where Aex is the absorbance at the excitation wavelength and Aem is the absorbance at the emission wavelength. The dissociation constant (Kd) was determined by the formula: 1/B=Kd/[free ligand]+1, where B is the fractional occupancy and [free ligand] is the concentration of free noscapine or 9-nitro-nos. The fractional occupancy (B) was determined by the formula B=ΔF/ΔFmax, where ΔF is the change in fluorescence intensity when tubulin and its ligand are in equilibrium and ΔFmax is the value of maximum fluorescence change when tubulin is completely bound with its ligand. ΔFmax was calculated by plotting $1/\Delta F$ versus 1/ligand using total ligand concentration as the first estimate of free ligand concentration.

Tubulin Polymerization Assay:

Mammalian brain tubulin (1.0 mg/ml) was mixed with different concentrations of 9-nitro-nos (25 or 100 µM) at 0° C. in an assembly buffer (100 mM PIPES at pH 6.8, 3 mM $MgSO_4$, 1 mM EGTA, 1 mM GTP, and 1M sodium glutamate). Polymerization was initiated by raising the temperature to 37° C. in a water bath. The rate and extent of the polymerization reaction were monitored by light scattering at 550 nm, using a 0.3-cm path length cuvette in a JASCO FP-6500 spectrofluorometer (JASCO, Tokyo, Japan) for 30 minutes.

In vitro Cell Proliferation Assays

Sulforhodamine B assay: The cell proliferation assay was performed in 96-well plates as described previously (Skehan et al., 1990; Zhou et al., 2003). Adherent cells (1A9 and 1A9/PTX22) were seeded in 96-well plates at a density of $5 \times 10^3$ cells per well. They were treated with increasing gradient concentrations of 9-nitro-nos the next day while in log-phase growth. After 72 hours of drug treatment, cells were fixed with 50% trichloroacetic acid and stained with 0.4% sulforhodamine B dissolved in 1% acetic acid. Cells were then washed with 1% acetic acid to remove unbound dye. The protein-bound dye was extracted with 10 mM Tris base to determine the optical density at 564-nm wavelength.

MTS Assay:

Suspension cells (CEM, CEMNLB100 and CEM/VM-1-5) were cultured in RPMI-1640 media containing 10% FBS and then seeded into 96-well plates at a density of $5 \times 10^3$ cells per well and were treated with increasing gradient concentrations of 9-nitro-nos for 72 hours. Measurement of cell proliferation was performed colorimetrically by 3-(4,5-dimethylthiazol-2-yl)-5-(3-carboxymethoxyphenyl)-2-(4-sulphophenyl)-2H-tetrazolium, inner salt (MTS) assay, using the CellTiter96 AQueous One Solution Reagent (Promega, Madison, Wis.). Cells were exposed to MTS for 3 hours and absorbance was measured using a microplate reader (Molecular Devices, Sunnyvale, Calif.) at an optical density (OD) of 490 nm. The percentage of cell survival as a function of drug concentration for both the assays was then plotted to determine the $IC_{50}$ value, which stands for the drug concentration needed to prevent cell proliferation by 50%.

Cell Cycle Analysis:

The flow cytometric evaluation of the cell cycle status was performed as described previously (Zhou et al., 2003). Briefly, $2 \times 10^6$ cells were centrifuged, washed twice with ice-cold PBS, and fixed in 70% ethanol. Tubes containing the cell pellets were stored at 4° C. for at least 24 hours. Cells were then centrifuged at 1000×g for 10 min and the supernatant was discarded. The pellets were washed twice with 5 ml of PBS and then stained with 0.5 ml of propidium iodide (0.1% in 0.6% Triton-X in PBS) and 0.5 ml of RNase A (2 mg/ml) for 45 minutes in dark. Samples were then analyzed on a FACSCalibur flow cytometer (Beckman Coulter Inc., Fullerton, Calif.).

Immunofluorescence Microscopy:

Cells adhered to poly-L-lysine coated coverslips were treated with 9-nitro-nos for 72 hours. After treatment, cells were fixed with cold (−20° C.) methanol for 5 min and then washed with phosphate-buffered saline (PBS) for 5 min. Non-specific sites were blocked by incubating with 100 µl of 2% BSA in PBS at 37° C. for 15 min. A mouse monoclonal antibody against α-tubulin (DM1A, Sigma) was diluted 1:500 in 2% BSA/PBS (100 µl) and incubated with the coverslips for 2 hours at 37° C. Cells were then washed with 2% BSA/PBS for 10 min at room temperature before incubating with a 1:200 dilution of a fluorescein-isothiocyanate (FITC)-labeled goat anti-mouse IgG antibody (Jackson ImmunoResearch, Inc., West Grove, Pa.) at 37° C. for 1 hour. Coverslips were then rinsed with 2% BSA/PBS for 10 min and incubated with propidium iodide (0.5 µg/ml) for 15 min at room temperature before they were mounted with Aquamount (Lerner Laboratories, Pittsburgh, Pa.) containing 0.01% 1,4-diazobicyclo(2,2,2)octane (DABCO, Sigma). Cells were then examined using confocal microscopy for microtubule morphology, and nuclear morphology to visualize DNA fragmentation (at least 100 cells were examined per condition).

Terminal Deoxynucleotidyl-Transferase-Mediated dUTP Nick-End Labeling (TUNEL) Assay for Apoptosis:

DNA strand breaks were identified by using the TUNEL assay as described. In brief, 1A9/PTX22 cells were incubated with 50 µM 9-nitro-nos for 72 hours. Cells were pelleted and washed with ice-cold PBS twice. Cells were then fixed in 1% paraformaldehyde, and apoptosis was detected using the APO-BrdU TUNEL Assay Kit from Molecular Probes (Eugene, Oreg.) according to the manufacturer's instructions. This assay was run on a flow cytometer equipped with a 488 nm argon laser as the light source. Propidium iodide (total cellular DNA) and Alexa-Fluor 488 (apoptotic cells) were the two dyes used. PI fluoresces at about 623 nm and Alexa-Fluor 488 at about 520 nm when excited at 488 nm. Single and dual parameter displays were created using the Cell Quest Data Acquisition Software (Becton Dickinson). The gating display was the standard dual parameter DNA doublet discrimination display with the DNA area signal on the Y-axis and the DNA width signal on the X-axis. From this display, a gate was generated around the non-clumped cells and the second gated dual parameter display was generated with the DNA (linear red fluorescence) on the X-axis and the Alexa-Fluor 488 (log green fluorescence) on the Y-axis. Apoptotic cells were subsequently counted as those expressing high Alexa-Fluor 488 fluorescence. Confocal micrographs were also obtained for the TUNEL-stained cells using a 63× objective.

Determination of caspase-3 activity: $10^6$ cells were incubated with 25 µM 9-nitro-nos (CEM, CEMNLB100 and CEM/VM-1-5) or 50 µM 9-nitro-nos (1A9 and 1A9/PTX22) for 0, 24, 48 and 72 hours. Caspase-3 activity was then measured by the cleavage of the small synthetic substrate Z-DEVD-aminoluciferin (CaspaseGlo™ 3/7 Assay System Kit, Promega, Madison, Wis.) that becomes luminogenic upon cleavage. The luminescent signal, which is directly proportional to the amount of caspase-3 activity, was measured in a luminescence plate reader.

Discussion

Introduction of a nitro moiety in place of a proton usually disrupts the tight interactions within the ligand-binding pockets of proteins. Therefore, the initial determination was whether 9-nitro-nos retains the tubulin binding activity of the parent compound, noscapine. Tubulin, like many other proteins, contains fluorescent amino acids like tryptophans and tyrosines. The intensity of the fluorescence emission is dependent upon the micro-environment around these amino acids in the folded protein. Agents that bind tubulin typically change the micro-environment and alter the fluorescent properties of the target protein (Ye et al., 1998; Peyrot et al., 1992; Panda et al., 1997). Measuring these fluorescent changes has become a relatively standard method for determining the binding properties of tubulin ligands including the classical compound colchicine (Peyrot et al., 1989; Andreu et al., 1991). Accordingly, this method was used to determine the dissociation constant (Kd) between tubulin and 9-nitro-nos, as compared to the carrier vehicle (DMSO). The results show that 9-nitro-nos quenched tubulin fluorescence in a saturable manner (FIG. 1B) and the double-reciprocal plot of these data revealed a Kd of 86±6 04 for 9-nitro-nos binding to tubulin (FIG. 1C).

9-nitro-nos Does not Affect the Assembly Rate and Steady State Monomer/Polymer tubulin mass.

The issue of whether 9-nitro-nos promoted or inhibited microtubule polymerization was then addressed. Noscapine does not significantly promote or inhibit microtubule polymerization upon binding tubulin, even at a concentration as high as 100 μM (Zhou et al., 2003). However, it does alter the steady-state dynamics of microtubule assembly, primarily by increasing the amount of time that the microtubules spend in an attenuated (pause) state (Zhou et al., 2002a). This property of noscapine makes it unique and has resulted in its extensive use to explore the role of microtubule dynamics during the spindle assembly checkpoint signaling. More importantly, it provides an advantage that post-mitotic cells like neurons do not get adversely affected by this drug even at higher concentrations. This is in contrast to the currently used anticancer drugs such as the family of taxanes and the vinca alkaloids, high micromolar concentrations of which cause devastating effects on cellular microtubules. Accordingly, the effect of 9-nitro-nos on the assembly of tubulin subunits into microtubules was evaluated in vitro by measuring the changes in the turbidity produced upon tubulin polymerization. The results show that 9-nitro-nos did not inhibit the rate or extent of tubulin polymerization at 25 μM or even at concentrations as high as 100 μM (FIG. 1D). Having identified tubulin as the target molecule, the pharmacology study was extended at the cellular level to determine mechanisms by which 9-nitro-nos affects the cell cycle and induces cell death.

9-nitro-nos Effectively Inhibits Proliferation of Cancer Cells Including Vinblastine-, Teniposide-, and Paclitaxel-resistant Variants.

Figure 2:
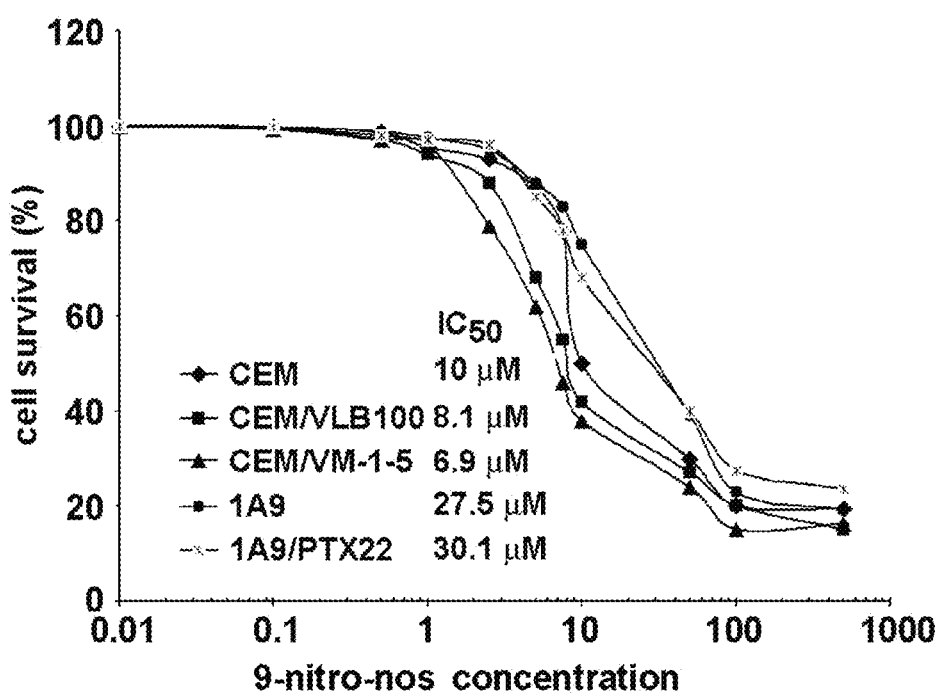
FIG. 2 is a graph showing that 9-nitro-nos actively inhibits the proliferation of various human cancer cells, including those that are resistant to vinblastine, teniposide and paclitaxel. CEM, CEMNLB100, CEM/VM-1-5, 1A9, 1A9/PTX22 cells were treated with 9-nitro-nos at gradient concentrations for 72 hours. The $IC_{50}$ value, which stands for the drug concentration needed to prevent cell proliferation by 50% was then measured using standard in vitro proliferation assays. The 3-(4,5-dimethylthiazol-2-yl)-5-(3-carboxymethoxyphenyl)-2-(4-sulphophenyl)-2H-tetrazolium salt (MTS) assay was used for non-adherent suspension cells (CEM, CEMNLB100 and CEM/VM-1-5) and the sulforhodamine B (SRB) assay was performed for adherent cells (1A9 and 1A9/PTX22). Each value represents average of two independent experiments with five replicates each.

Although many microtubule-binding drugs are active against many tumor types, however, most of these agents fail to manage the drug-resistant phenotypes of recurrent tumors. One major mechanism of acquired drug resistance is the overexpression of efflux pumps, namely, P-gp170/MDR and MRP. For example, CEMNLB100 cells, the pgp-overexpressing vinblastine-resistant variants show a 270-fold resistance to vinblastine (Beck and Cirtain, 1982) and CEM/VM-1-5 cells, the MRP-overexpressing variants display a 400-fold resistance to teniposide (Morgan et al., 2000). Surprisingly, 9-nitro-nos is active against the parental CEM cells and those of CEM-derived vinblastine- and teniposide-resistant cells despite pgp or MRP overexpression. In an in vitro cell proliferation MTS assay to determine the drug concentration required to inhibit cell growth by 50% after incubation in the culture medium for 72 hours, we found that the median inhibitory concentration ($IC_{50}$) of 9-nitro-nos for CEM, CEM/VLB100 and CEM/VM-1-5 cells was 10 μM, 8.1 μM and 6.9 μM □ respectively (FIG. 2). It is worth mentioning that the $IC_{50}$ value for the drug-resistant sub-lines is lower than the parent line.

The effect of 9-nitro-nos on ovarian cancer cells, 1A9 and its paclitaxel-resistant variant, 1A9/PTX22 (Giannakakou et al., 1997) was then evaluated. Using a standard sulforhodamine B assay to evaluate percent cell survival for these adherent cells, the $IC_{50}$ value was 30.1 μM and 27.5 μM for 1A9, the parent ovarian cancer cells and 1A9/PTX22, the paclitaxel-resistant variants respectively (FIG. 2). In the ovarian cancer cells also, it was determined that the $IC_{50}$ value for the drug-resistant variant was lower than the parent cells, suggesting increased sensitivity. All cell types and their normal counterparts included in the study are listed in Table 1.

TABLE 1

Effect of 9-nitro-nos on cell cycle progression of drug-resistant cell lines and their normal counterparts. Cells were treated with 9-nitro-nos for the indicated times before being stained with propidium iodide for cell cycle analysis.

| Cell Cycle Parameters | CEM | | | | CEM/VLB100 | | | | CEM/VM-1-5 | | | | 1A9 | | | | 1A9/PTX22 | | | |
|---|---|---|---|---|---|---|---|---|---|---|---|---|---|---|---|---|---|---|---|---|
| | 0 h | 24 h | 48 h | 72 h | 0 h | 24 h | 48 h | 72 h | 0 h | 24 h | 48 h | 72 h | 0 h | 24 h | 48 h | 72 h | 0 h | 24 h | 48 h | 72 h |
| $G_0/G_1$ | 45.5 | 24.8 | 19.7 | 13.9 | 46.9 | 25.5 | 23.7 | 8.7 | 36.0 | 25.4 | 13.7 | 10.5 | 50.0 | 30.6 | 28.6 | 16.7 | 57.0 | 27.3 | 5.9 | 14.1 |
| S | 25.0 | 10.0 | 8.1 | 8.9 | 17.6 | 17.7 | 9.3 | 4.5 | 19.4 | 13.0 | 11.0 | 8.7 | 21.8 | 14.3 | 10.6 | 9.6 | 8.8 | 4.7 | 3.4 | 5.7 |
| $G_2/M$ | 20.9 | 34.2 | 40.0 | 16.9 | 25.7 | 36.0 | 30.2 | 12.5 | 30.7 | 41.0 | 15.0 | 12.2 | 21.2 | 34.2 | 17.2 | 9.0 | 20.4 | 31.4 | 44.3 | 13.7 |
| Sub-$G_1$ | 0.25 | 6.5 | 23.8 | 44.3 | 3.6 | 14.8 | 30.7 | 56.1 | 3.4 | 18.8 | 58.0 | 63.0 | 0.7 | 12.0 | 38.0 | 56.3 | 3.5 | 30.0 | 44.6 | 59.0 |

9-nitro-nos Alters Cell Cycle Profile and Induces G2/M Arrest in Cancer Cells

Figure 3:
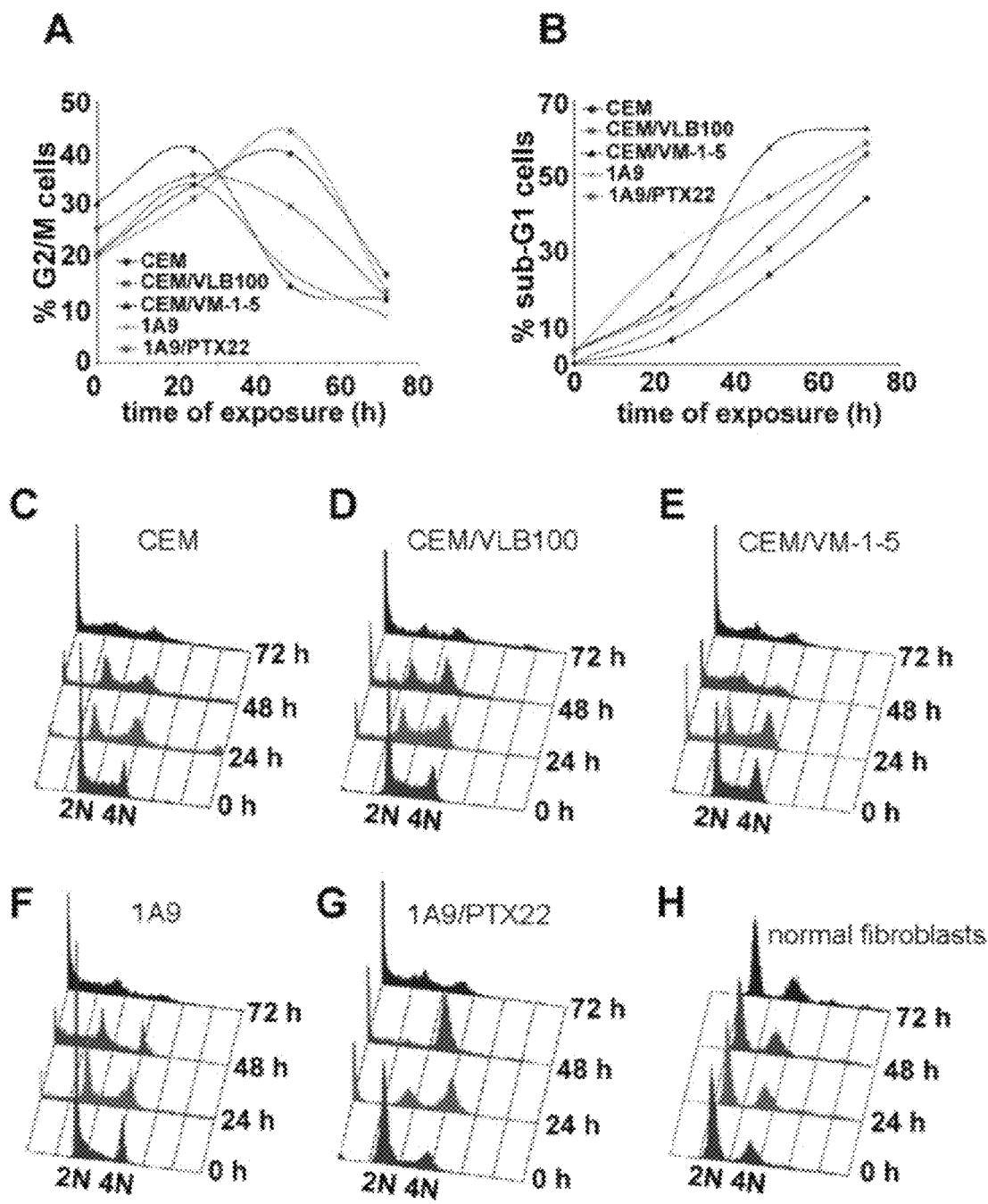
FIGS. 3 A and B represent the mitotic and apoptotic index as a function of time of treatment with 9-nitro-nos.

Microtubule-interfering agents, including noscapine (Ye et al., 1998; Zhou et al., 2002a) are well-known to arrest cell cycle progression at the G2/M phase in mammalian cells (Jordan and Wilson, 1999). Therefore, the effect of 9-nitro-nos on the mitotic index and apoptotic index of these cancer cells as a function of time was evaluated. As can be seen in FIG. 3A, mitotic figures peak at about 24-48 hours of drug exposure and then decline up to 72 hours of observation. Consistent with this, the apoptotic cells rise in number during this time (FIG. 3B). Fluorescently labeled DNA accumulation is a good indicator of cell cycle progression and cell death. An unreplicated complement of 2N DNA cells represents the G1 phase while duplicated 4N DNA cells represent G2 and M phases. Cells in the process of DNA duplication between 2N and 4N peaks represent the S phase. Less than 2N DNA appears in populations of dying cells that degrade their DNA to different extents. FIG. 3(C-G) depict the flow cytometric profile of CEM, CEMNLB100, CEM/VM-1-5, 1A9, 1A9/PTX22 cells, respectively, treated with 9-nitro-nos for 0, 24, 48 and 72 hours. The concentration of 9-nitro-nos used for the cell cycle study was 25 μM for CEM, CEMNLB1000 and CEM/VM-1-5 cells. 50 μM 9-nitro-nos concentration was used for 1A9 and 1A9/PTX22 cells. As is clearly evident from the three-dimensional FACS profiles, the display of DNA content as a function of time of drug exposure shows pronounced increase in the population of cells that accumulate with less than 2N DNA (sub-G1 population) at 72 hours indicating dying cells. This is preceded by an accumulation of cell populations with 4N DNA indicating G2/M arrest. The anticancer activity of 9-nitro-nos treatment was thus evident in its ability to produce a significant sub-G1 population, representing the fraction of cells which have hypodiploid (<2N) DNA content, typifying a cell population having degraded DNA, a characteristic of apoptosis. The effect of 9-nitro-nos on the progression of the entire cell cycle as a function of time shown as the percentage of G0/G1, S, G2/M and sub-G1 populations in all three lymphoma cell lines and the two ovarian cell lines is shown in Table 2.

TABLE 2

$IC_{50}$ values of halogenated derivatives of noscapine

| | IC50(μM) | | | |
|---|---|---|---|---|
| | Nos | 9-F-nos | 9-Br-nos | 9-I-nos |
| MCF-7 | 39.6 ± 2.2 | 3.3 ± 0.8 | 1.0 ± 0.2 | 45.6 ± 3.1 |
| MDA-MB-231 | 36.3 ± 1.8 | 8.2 ± 0.6 | 3.3 ± 0.4 | 25.6 ± 2.4 |
| CEM | 16.6 ± 2.4 | 2.3 ± 0.7 | 1.9 ± 0.2 | 38.9 ± 3.5 |

Since the progression of normal cells through the cell cycle is tightly regulated by checkpoints, ensuring exact replication of the genome during the S-phase and its precisely equal division at mitosis, we investigated whether 9-nitro-nos affects the cell cycle of the normal human fibroblast cells. Surprisingly, we did not observe any perturbations in the cell cycle profile of normal fibroblast cells at even 100 μM 9-nitro-nos (FIG. 3H). Thus, in vitro studies with normal human cell cultures that show resistance to the apoptotic effects of 9-nitro-nos are in contrast to the adverse effects seen with human cancer cells. This selectivity towards cancer cells places 9-nitro-nos uniquely over most of the currently used conventional chemotherapeutic agents, which lack specificity for dividing cells.

Nevertheless, the cell cycle analyses suggest that the lymphoma and the ovarian cancer cells including their drug-resistant variants succumb to apoptosis upon treatment with 9-nitro-nos. Therefore, a variety of apoptotic events were evaluated using several complementary cytometric and biochemical methods.

9-nitro-nos Causes Extensive Apoptosis as Revealed by Immunocytochemistry

Figure 4:
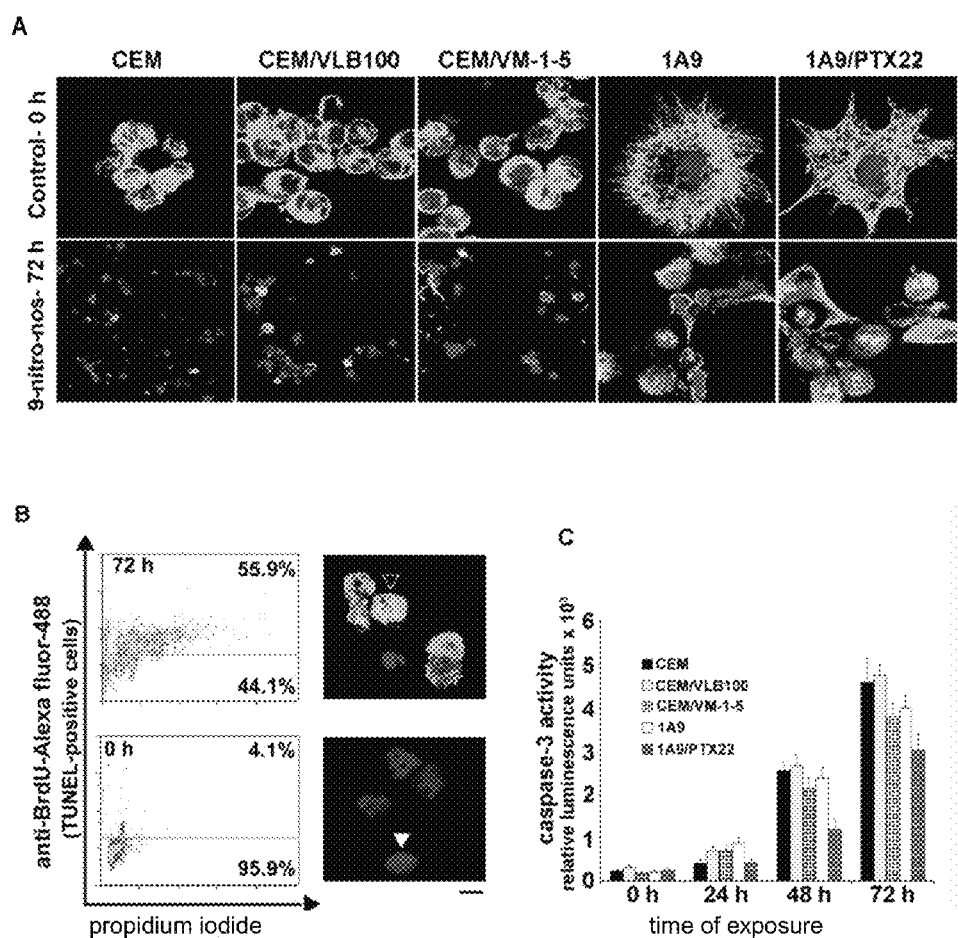
FIG. 4A is a series of photographs showing that 9-nitro-nos selectively kills cancer cells by inducing apoptosis, as demonstrated by devastating changes in the nuclear morphology of these cells. The top panel shows untreated cells that display normal microtubule arrays. 9-nitro-nos treatment for 72 hours completely devastates the morphologies, as shown by the fragmented condensed apoptotic bodies (FIG. 4 A, bottom panel). (Scale bar=20 μM).
FIG. 4B is a chart showing the fragmented DNA in the terminal stages of apoptosis, as measured using a flow-cytometry based quantitative terminal deoxynucleotidyl transferase (TdT)-mediated bromo-deoxyuridine triphosphate (BrdUTP) reaction (TUNEL assay) in a representative cell line (1A9/PTX22). Untreated control cells are shown in the lower panel and 50 μM 9-nitro-nos treated 1A9/PTX22 cells are shown in the upper panel. After 72 hours of 9-nitro-nos treatment, cells were processed for apoptosis by a flow cytometry-based terminal deoxynucleotidyl transferase (TdT)-mediated bromo-deoxyuridine triphosphate (BrdUTP) reaction. Addition of BrdUTP to the TdT reaction provides a means to label the DNA strand breaks, and is detected by an Alexa Fluor 488 labeled anti-BrdU antibody. DNA content was determined by the binding of DNA specific dye, propidium iodide (x-axis). Apoptotic cells were determined by incorporation of BrdU at the 3'-OH ends of the fragmented DNA as measured by anti-BrdU Alexa Fluor 488 labeled antibody on the y-axis. The number of apoptotic cells is indicated by the number of Alexa Fluor 488 positive cells of the total gated cells. The fragmented DNA was also visualized using confocal microscopy as an abundance of TUNEL-positive cells (upper right panel, open arrowhead). Untreated control cells appear red (lower right panel, solid arrowhead) (Scale bar=20 μM). Data shown are from a representative experiment of two experiments performed.
FIG. 4C is a chart showing that 9-nitro-nos treatment causes activation of caspase-3. The chart shows the time-dependent increase (in hours) in caspase-3 activity on 9-nitro-nos treatment in CEM, CEM/VLB100, CEM/VM-1-5, 1A9 and 1A9/PTX22 cells. After drug incubation, caspase-3 activity was analyzed using the luminogenic substrate Z-DEVD-aminoluciferin.

The onset of apoptosis characteristically changes cellular morphology. This includes membrane blebbing, formation of apoptotic bodies, disruption of cytoskeleton, and hypercondensation and fragmentation of chromatin. To visualize this, control untreated cells as well as cells treated with 9-nitro-nos for 72 hours were analyzed by immunocytochemistry using a tubulin-specific antibody (green) and a DNA-binding dye (red). Confocal micrographs (FIG. 4A, top panel) shows control untreated CEM, CEM/VLB100, CEM/VM-1-5, 1A9 and 1A9/PTX22 cells. As expected, untreated control cells show normal radial microtubule arrays. In contrast, both lymphoma cells and ovarian cancer cells treated with 9-nitro-nos for 72 hours show extensive terminal apoptotic figures with fragmented DNA pieces and perturbed microtubule arrays (FIG. 4A, bottom panels).

9-nitro-nos Treatment Caused DNA Fragmentation as Measured Quantitatively by a Flow Cytometry Based TUNEL Analysis To further establish the apoptotic mechanism of cell death quantitatively, we next performed a flow cytometry based TUNEL assay in 1A9/PTX22 cells treated with 9-nitro-nos for 72 hours. Since the end stages of apoptosis display cleaved 3'-ends of DNA, they can be visualized by specific labeling using TUNEL assay as an abundant green staining (FIG. 4B, upper right panel, open arrowheads, red denotes PI staining)

The quantitative FACS analysis showed 55.9% TUNEL-positive cells within a population of 1A9/PTX22 cells treated with 50 μM 9-nitro-nos for 72 hours (FIG. 4B, upper left panel). In contrast, control untreated cells only occasionally show TUNEL-staining and TUNEL-negative cells appear red (FIG. 4B, lower right panel, solid arrowhead). This is consistent with the quantitative FACS data that depict 95.9% control cells containing intact genomic DNA in the lower region of the cytogram representing the TUNEL-negative cells (FIG. 4B, lower left panel). The other cell lines also showed similar results (data not shown).

9-nitro-nos Causes Activation of Caspase-3, a Hallmark of Apoptosis, as a Function of Time Caspases, the cysteine proteases, have been implicated as key participants in the sequence of events that result in the dismantling of the cell during apoptosis. The activation of caspase-3 is caused by upstream caspases and involves the cleavage of the inactive proenzyme into an active form. The active form can be monitored using a small peptide substrate which becomes luminogenic upon cleavage. As shown in FIG. 4C, a concomitant time-dependent activation of caspase-3 as much as 10-20 fold was observed in both the lymphoma cells and ovarian cancer cells including their drug-resistant variants upon 72 hours of 9-nitro-nos treatment.

Conclusions

Microtubule-interacting agents, both that polymerize and bundle microtubule (such as taxanes) or those that depolymerize and decrease polymer mass (such as vincas) have been useful for the treatment of many cancer types. Unfortunately, the clinical success of these agents has been severely hampered by the emergence of drug resistant tumor cells and associated toxicities. A coupled aspect of the toxicity manifestation is their lack of specificity for dividing cells. Therefore, there has been a tremendous interest in identifying novel antimicrotubule agents that overcome various modes of resistance, display selectivity for cancer cells and have safer pharmacology profiles. The data clearly demonstrate that 9-nitro-nos effectively inhibits cellular proliferation of lymphoma and ovarian cancer cells, in particularly those that overexpress multidrug resistant proteins. Furthermore, 9-nitro-nos significantly arrest cells at the G2/M phase of the cell cycle followed by apoptotic cell death, as revealed by several prototypic features of apoptosis. Interestingly, unlike currently used chemotherapeutics, 9-nitro-nos does not affect the cell cycle of normal human fibroblast cells. These findings thus indicate a great potential for the use of 9-nitro-nos as a chemotherapeutic agents for the treatment of human cancers, especially for those that are resistant to currently used microtubule drugs.

REFERENCES

Andreu J M, Gorbunoff M J, Medrano F J, Rossi M and Timasheff S N (1991) Mechanism of colchicine binding to tubulin. Tolerance of substituents in ring C' of biphenyl analogues. Biochemistry 30:3777-3786.

Beck W T and Cirtain M C (1982) Continued expression of vinca alkaloid resistance by CCRF-CEM cells after treatment with tunicamycin or pronase. Cancer Res 42:184-189.

Crivello J V (1981) Nitrations and oxidations with inorganic nitrate salts in trifluoroacetic anhydride. J Org Chem 46:3056-3060.

Crown J and O'Leary M (2000) The taxanes: an update. Lancet 355:1176-1178.

Dahlstrom B, Mellstrand T, Lofdahl C G and Johansson M (1982) Pharmacokinetic properties of noscapine. Eur J Clin Pharmacol 22:535-539.

Desai A and Mitchinson T J (1997) Microtubule polymerization dynamics Annu Rev Cell Dev Biol 13:83-117.

Dumontet C, Isaac S, Souquet P J, Bejui-Thivolet F, Pacheco Y, Peloux N, Frankfurter A, Luduena R and Perol M (2005) Expression of class III beta tubulin in non-small cell lung cancer is correlated with resistance to taxane chemotherapy. Bull Cancer 92:E25-30.

Giannakakou P, Sackett D L, Kang Y K, Zhan Z, Buters J T, Fojo T and Poruchynsky M S (1997) Paclitaxel-resistant human ovarian cancer cells have mutant beta-tubulins that exhibit impaired paclitaxel-driven polymerization. J Biol Chem 272:17118-17125.

Gupta K and Panda D (2002) Perturbation of microtubule polymerization by quercetin through tubulin binding: a novel mechanism of its antiproliferative activity. Biochemistry 41:13029-13038.

Jensen L N, Christrup L L, Jacobsen L, Bonde J and Bundgaard H (1992) Relative bioavailability in man of noscapine administered in lozenges and mixture. Acta Pharm Nord 4:309-312.

Jordan M A and Wilson L (1999) The use and action of drugs in analyzing mitosis. Methods Cell Biol 61:267-291.

Jordan M A and Wilson L (2004) Microtubules as a target for anticancer drugs. Nat Rev Cancer 4:253-265.

Joshi H C (1998) Microtubule dynamics in living cells. Curr Opin Cell Biol 10:35-44.

Joshi H C and Zhou J (2001) Gamma tubulin and microtubule nucleation in mammalian cells. Methods Cell Biol 67:179-193.

Karlsson M O, Dahlstrom B, Eckernas S A, Johansson M and Alm A T (1990) Pharmacokinetics of oral noscapine. Eur J Clin Pharmacol 39:275-279.

Kirschner M and Mitchison T J (1986) Beyond self-assembly: From microtubules to morphogenesis. Cell 45:329-342.

Landen J W, Hau V, Wang M S, Davis T, Ciliax B, Wainer B H, Van Meir E, G, Glass J D, Joshi H C and Archer D R (2004) Noscapine crosses the blood-brain barrier and inhibits glioblastoma growth. Clin Cancer Res 10:5187-5201.

Landen J W, Lang R, McMahon S J, Rusan N M, Yvon A M, Adams A W, Sorcinelli M D, Campbell R, Bonaccorsi P, Ansel J C, Archer D R, Wadsworth P, Armstrong C A and Joshi H C (2002) Noscapine alters microtubule dynamics in living cells and inhibits the progression of melanoma. Cancer Res 62:4109-4114.

Lee D-U (2002) (−)-□-Narcotine: a facile synthesis and the degradation with ethyl chloroformate. Bull Korean Chem Soc 23:1548-1552.

Margolis R L and Wilson L (1981) Microtubule treadmills-possible molecular machinery. Nature 293:705-711.

Margolis R L and Wilson L (1998) Microtubule tread milling: what goes around comes around. Bioessays 20:830-836.

McIntosh J R (1994) The role of microtubules in chromosome movement, in Microtubules (Hyams J S and Lloyd C W eds) pp 413-434, Wiley-Liss, New York.

Mitchison T J and Kirschner M (1984) Dynamic instability of microtubule growth. Nature 312:237-242.

Monzo M, Rosell R, Sanchez J J, Lee J S, O'Brate A, Gonzalez-Larriba J L, Alberola V, Lorenzo J C, Nunez L, Ro J Y and Martin C (1999) Paclitaxel resistance in non-small-cell lung cancer associated with beta-tubulin gene mutations. J Clin Oncol 17:1786-1793.

Morgan S E, Kim R, Wang P C, Bhat U, Kusumoto H, Lu T and Beck W T (2000) Differences in mutant p53 protein stability and functional activity in teniposide-sensitive and -resistant human leukemic CEM cells compared with parental CEM cells. Oncogene 19:5010-5019.

Nogales E (2000) Structural insights into microtubule function Annu Rev Biochem 69:277-302.

Pace A, Bove L, Nistico C, Ranuzzi M, Innocenti P, Pietrangeli A, Terzoli E, and Jandolo B (1996) Vinorelbine neurotoxicity: clinical and neurophysiological findings in 23 patients. J Neurol Neurosurg Psychiatry 61:409-411.

Panda D, Chakrabarti G, Hudson J, Pigg K, Miller H P, Wilson L and Himes R H (2000) Suppression of microtubule dynamic instability and tread milling by deuterium oxide. Biochemistry 39:5075-5081.

Panda D, Singh J P and Wilson L (1997) Suppression of microtubule dynamics by LY290181. J Biol Chem 272:7681-7687.

Peyrot V, Leynadier D, Sarrazin M, Briand C, Menendez M, Laynez J and Andreu J M (1992) Mechanism of binding of the new antimitotic drug MDL 27048 to the colchicine site of tubulin: equilibrium studies. Biochemistry 31:11125-11132.

Peyrot V, Leynadier D, Sarrazin M, Briand C, Rodriquez A, Nieto J M and Andreu J M (1989) Interaction of tubulin and cellular microtubules with the new antitumor drug MDL 27048. A powerful and reversible microtubule inhibitor. J Biol Chem 264:21296-21301.

Ranganathan S, Dexter D W, Benetatos C A, Chapman A E, Tew K D and Hudes G R (1996) Increase of beta(III)- and beta(IVa)-tubulin isotypes in human prostate carcinoma cells as a result of estramustine resistance. Cancer Res 56:2584-2589.

Rowinsky E K (1997) The development and clinical utility of the taxane class of antimicrotubule chemotherapy agents. Annu Rev Med 48:353-374.

Sammak P J and Borisy G G (1987) Direct observation of microtubule dynamics in living cells. Nature 332:724-726.

Skehan P, Storeng R, Scudiero D, Monks A, McMahon J, Vistica D, Warren J T, Bokesch H, Kenney S and Boyd M R (1990) New colorimetric cytotoxicity assay for anticancer-drug screening. J Natl Cancer Inst 82:1107-1112.

Theiss C and Meller K (2000) Taxol impairs anterograde axonal transport of microinjected horseradish peroxidase in dorsal root ganglia neurons in vitro. Cell Tissue Res 299:213-224.

Topp K S, Tanner K D, and Levine J D (2000) Damage to the cytoskeleton of large diameter sensory neurons and myelinated axons in vincristine-induced painful peripheral neuropathy in the rat. J Comp Neurol 424:563-576.

Ye K, Ke Y, Keshava N, Shanks J, Kapp J A, Tekmal R R, Petros J and Joshi H C (1998) Opium alkaloid noscapine is an antitumor agent that arrests metaphase and induces apoptosis in dividing cells. Proc Natl Acad Sci USA 95:1601-1606.

Zhou J, Gupta K, Aggarwal S, Aneja R, Chandra R, Panda D and Joshi H C (2003) Brominated derivatives of noscapine are potent microtubule-interfering agents that perturb mitosis and inhibit cell proliferation. Mol Pharmacol 63:799-807.

Zhou J, Gupta K, Yao J, Ye K, Panda D, Giannakakou P and Joshi H C (2002b) Paclitaxel-resistant human ovarian cancer cells undergo c-Jun NH2-terminal kinase-mediated apoptosis in response to noscapine. J Biol Chem 277:39777-39785.

Zhou J, Panda D, Landen J W, Wilson L and Joshi H C (2002a) Minor alteration of microtubule dynamics causes loss of tension across kinetochore pairs and activates the spindle checkpoint. J Biol Chem 277:17200-17208.

Example 3

Synthesis of Halogenated Noscapine Analogues (S)-3-(R)-9-bromo-4-methoxy-6-methyl-5,6,7,8-tetrahydro-[1,3]dioxolo[4,5-g]isoquino-lin-5-yl)-6,7-dimethoxy-isobenzofuran-1 (3H)-one:

To a flask containing noscapine (20 g, 48.4 mmol) was added minimum amount of 48% hydrobromic acid solution (~40 ml) to dissolve or make a suspension of the reactant. To the reaction mixture was added freshly prepared bromine water (~250 ml) drop wise until an orange precipitate appeared. The reaction mixture was then stirred at room temperature for 1 h to attain completion, adjusted to pH 10 using ammonia solution to afford solid precipitate. The solid precipitate was recrystallized with ethanol to afford bromo-substituted noscapine. Yield: 82%; mp 169-170° C.; IR: 2945 (m), 2800 (m), 1759 (s), 1612 (m), 1500 (s), 1443 (s), 1263 (s), 1091 (s), 933 (w) cm$^{-1}$; $^1$H NMR (CDCl$_3$, 400 MHz), δ 7.04 (d, 1H, J=7 Hz), 6.32 (d, 1H, J=7 Hz), 6.03 (s, 2H), 5.51 (d, 1H, J=4 Hz), 4.55 (d, 1H, J=4 Hz), 4.10 (s, 3H), 3.98 (s, 3H), 3.89 (s, 3H), 2.52 (s, 3H), 2.8-1.93 (m, 4H); $^{13}$C NMR (CDCl$_3$, 100 MHz), δ 167.5, 151.2, 150.5, 150.1, 148.3, 140.0, 135.8, 130.8, 120.3, 120.4, 120.1, 105.3, 100.9, 100.1, 87.8, 64.4, 56.1, 56.0, 55.8, 51.7, 41.2, 27.8; MS (FAB): m/z (relative abundance, %), 494 (93.8), 492 (100), 300 (30.5), 298 (35.4); MALDI: m/z 491.37 (M+), 493.34; ESI/tandem mass spectrometry: parent ion masses, 494, 492; daughter ion masses (intensity, %), 433 (51), 431 (37), 300 (100), 298 (93.3); HRMS (ESI): m/z Calcd. for $C_{22}H_{23}BrNO_7$ (M+1), 493.3211. Found, 493.3215 (M+1).

(S)-3-(R)-9-fluoro-4-methoxy-6-methyl-5,6,7,8-tetrahydro-[1,3]dioxolo[4,5-g]isoquino-lin-5-yl)-6,7-dimethoxyisobenzofuran-1 (3H)-one To a solution of bromonoscapine (1 g, 2.42 mmol) in anhydrous THF (20 ml) was added an excess of Amberlyst-A 26 (fluorine, polymer-supported, 2.5 g, 10 mequiv. of dry resin, the average capacity of the resin is 4 mequiv. per gram) and the reaction mixture refluxed for 12 hours. The resin was filtered off and the solvent removed to afford the crude product which was purified by flash column chromatography (ethyl acetate/hexane=4:1) to afford (S)-3-(R)-9-fluoro-4-methoxy-6-methyl-5,6,7,8-tetrahydro-[1,3]dioxolo[4,5-g]isoquinolin-5-yl)-6,7-dimethoxy-isobenzo-furan-1 (3H)-one (3) as a light brown crystals. The recovery of resin was achieved by washing with 1 M NaOH and then rinsing thoroughly with water until neutrality to afford hydroxy-form of resin. It was then stirred overnight with 1 M aqueous hydrofluoric acid (250 ml), washed with acetone, ether and dried in a vacuum oven at 50° C. for 12 hours to afford the regenerated Amberlyst-A 26 (fluorine, polymer-supported). Yield: 74%, light brown crystals; mp 170.8-171.1° C.; $^1$H NMR (CDCl$_3$, 400 MHz): δ 7.11 (d, 1H, J=8.0 Hz), 6.99 (d, 1H, J=8.0 Hz), 5.44 (s, 2H), 5.21 (d, 1H, J=4.1 Hz), 4.02 (d, 1H, J=4.1 Hz), 3.95 (s, 3H), 3.78 (s, 3H), 3.64 (s, 3H), 2.65-2.62 (m, 2H), 2.51-2.47 (m, 2H), 2.30 (s, 3H); $^{13}$C NMR (CDCl$_3$, 100 MHz): δ 167.5, 152.9, 148.4, 139.8, 134.5, 126.0, 121.8, 119.0, 108.8, 103.1, 93.8, 81.9, 64.8, 61.1, 59.7, 57.7, 55.0, 46.4, 45.8, 39.4, 20.7, 19.1; HRMS (ESI): m/z Calcd. for $C_{22}H_{23}FNO_7$ (M+1), 432.4192. Found, 432.4196 (M+1).

(S)-3-(R)-9-iodo-4-methoxy-6-methyl-5,6,7,8-tetrahydro-[1,3]dioxolo[4,5-g]isoquino-lin-5-yl)-6,7-dimethoxyisobenzofuran-1 (3H)-one The iodination of noscapine was achieved using pyridine-iodine chloride. Since this is not commercially available, we first prepared the said reagent using the following procedure. Iodine chloride (55 ml, 1 mol) was added to a solution of potassium chloride (120 g, 1.6 mol) in water (350 ml). The volume was then adjusted to 500 ml to give a 2 M solution. In the event the iodine chloride was under or over chlorinated, the solution was either filtered or the calculated quantity of potassium iodide added. Over chlorination was more to be avoided than under chlorination since iodine trichloride can serve as a chlorinating agent. Alternatively, the solution of potassium iododichloride was made as follows. A mixture of potassium iodate (71 g, 0.33 mol), potassium chloride (40 g, 0.53 mol) and conc. hydrochloric acid (5 ml) in water (80 ml) was stirred vigorously and treated simultaneously with potassium iodide (111 g, 0.66 mol) in water (100 ml) and with conc. hydrochloric acid (170 ml). The rate of addition of hydrochloric acid and potassium iodide solutions were regulated such that no chlorine was evolved. After addition was completed, the volume was brought to 500 ml with water to give a 2 N solution of potassium iododichloride, which itself is a very good iodinating agent. However, usage of reagent in the aromatic iodination of noscapine resulted in hydrolysis products due to the acidic nature of the reagent.

In an effort to minimize or avoid hydrolysis, a basic iodinating reagent, pyridine-iodine chloride was prepared as follows. To a stirred solution of pyridine (45 ml) in water (1 L) was added 2 M solution of potassium iododichloride (250 ml). A cream colored solid separated, the pH of the mixture was adjusted to 5.0 with pyridine and the solid collected by filtration, washed with water and air-dried to afford the pyridine-iodine chloride reagent in 97.5% yield (117 g) that was crystallized from benzene to afford light yellow solid.

Iodination of noscapine was now carried out by addition of pyridine-iodine chloride (1.46 g, 6 mmol) to a solution of noscapine (1 g, 2.42 mmol) in acetonitrile (20 ml) and the resultant mixture was stirred at room temperature for 6 hours and then at 100° C. for 6 hours. After cooling, excess ammonia was added and filtered through celite pad to remove the black nitrogen triiodide. The filtrate was made acidic with 1 M HCl and filtered to collect the yellow solid, washed with water and air-dried to afford (S)-3-(R)-9-iodo-4-methoxy-6-methyl-5,6,7,8-tetrahydro-[1,3]dioxolo[4,5-g]isoquinolin-5-yl)-6,7-dimethoxyisobenzofuran-1 (3H)-one (5). Yield: 76%, mp 172.3-172.6° C.; $^1$H NMR (CDCl$_3$, 400 MHz): δ 7.15 (d, 1H, J=8.1 Hz), 7.01 (d, 1H, J=8.1 Hz), 6.11 (s, 2H), 5.36 (d, 1H, J=4.8 Hz), 4.25 (d, 1H, J=4.8 Hz), 3.85 (s, 3H), 3.74 (s, 3H), 3.72 (s, 3H), 2.78-2.72 (m, 2H), 2.55-2.50 (m, 2H), 2.32 (s, 3H); $^{13}$C NMR (CDCl$_3$, 100 MHz): δ 168.2, 155.1, 151.5, 148.3, 146.5, 143.1, 140.3, 120.4, 119.5, 113.3, 101.5, 85.9, 82.2, 61.8, 56.6, 55.7, 54.5, 54.1, 51.2, 39.8, 30.1, 18.8; HRMS (ESI): m/z Calcd. for $C_{22}H_{23}INO_7$ (M+1), 540.3209. Found, 540.3227 (M+1).

HPLC Purity and Peak Attributions:

Method 1: Ultimate Plus, LC Packings, Dionex, C18 column (pep Map 100, 3 μm, 100 Å particle size, ID: 1000 μm, length: 15 cm) with solvent systems A (0.1% formic acid in water) and B (acetonitrile), a gradient starting from 100% A and 0% B to 0% A and 100% B over 25 min at a flow of 40 μL/min (Table 1).

Method 2: Ultimate Plus, LC Packings, Dionex, C18 column (pep Map 100, 3 μm, 100 Å particle size, ID: 1000 μm, length: 15 cm) with solvent systems A (0.1% formic acid in water) and B (methanol), a gradient starting from 100% A and 0% B to 0% A and 100% B over 25 min at a flow of 40 µL/min (Table 1).

Other Findings Related to Noscapine Halogenation

Aromatic halogenation constitutes one of the most important reactions in organic synthesis. Although, bromine is extensively used for carrying out electrophilic aromatic substitution reactions in the presence of iron bromide or aluminum chloride, its utility is limited because of the practical difficulty in handling this reagent in laboratories, compared to N-bromo-(NBS). Thus, NBS has proven to be a superior halogenating reagent provided benzylic bromination is suppressed. For example, Schmid reported that benzene and toluene gave nuclear brominated derivatives in good yields with NBS and $AlCl_3$ without solvents under long reflux using a large amount of the catalyst (>1 equiv) [30]. However, reactions using NBS in the presence of $H_2SO_4$, $FeCl_3$, and $ZnCl_2$ resulted in relatively low yields (21-61%) together with the polysubstituted products. In another report by Lambert et al., aromatic substituted derivatives were obtained in good yields with NBS in 50% aqueous $H_2SO_4$ [31], however, this method required considerably high acidic conditions which are not suitable for acid labile compounds, such as noscapine. Thus, there still exists a need to develop selective, reproducible and efficient procedures for the halogenation of such labile aromatic compounds that eliminate the limitations associated with the above discussed synthetic methods and offer quantitative yields of the desired compounds. Noscapine consists of isoquinoline and benzofuranone ring systems joined by a labile C—C chiral bond and both these ring systems contain several vulnerable methoxy groups. Thus, achieving selective halogenation at C-9 position without disruption and cleavage of these labile groups and C—C bonds was challenging. After careful titration of many conditions, simple, selective, efficient, and reproducible synthetic procedures have been developed to achieve halogenation at C-9 position. These procedures are discussed below.

First, the bromination of noscapine with bromine water in the presence of HBr was examined (Scheme 1). 9-Br-nos, (2) was prepared as described previously with minor modifications [12,32]. Noscapine (1) was dissolved in minimum amount of 48% hydrobromic acid with continuous stirring followed by the addition of freshly prepared bromine water over a period of 1 hour until the appearance of an orange precipitate. The reaction mixture was then stirred at room temperature for 1 hour to attain completion. Next, the resultant mixture was adjusted to pH 10 using ammonia solution to obtain 9-Br-nos (2) in 82% yield. Excess amount of HBr or longer reaction times were avoided because they resulted in the hydrolyzed products, meconine and cotamine. The bromination took place selectively on ring A of isoquinoline nucleus at position C-9. An absence of C-9 aromatic proton at δ 6.30-ppm in the $^1H$ NMR spectrum of the product confirmed bromination at C-9 position. $^{13}C$ NMR and HRMS data support the structure of the compound.

Aromatic fluorination of noscapine was achieved by employing the fluoride form of Amberlyst-A 26, a macroreticular anion-exchange resin containing quaternary ammonium groups. The method described [33] for Hal/F exchange may also be applied to other Hal/Hal' exchange reactions. In Br/F exchange reactions, good yields were obtained only when a large molar ratio of the resin with respect to the substrate was employed. Thus, after refluxing a solution of bromonoscapine in anhydrous THF and an excess of Amberlyst-A 26 (fluorine, polymer-supported, 10 milliequivalents of dry resin; the average capacity of the resin is 4 milliequivalents per gram) for 12 hours, the resin was filtered off and the solvent was removed in vacuo to afford the desired compound (3) in 74% yield. The resin was recovered by washing with 1 N NaOH and then rinsing thoroughly with water until neutrality to generate the hydroxy-form of the resin. It was then stirred overnight with 1 N aqueous hydrofluoric acid, washed with acetone, ether and dried in a vacuum oven at 50° C. for 12 hours to afford the regenerated Amberlyst-A 26 (fluorine, polymer-supported), which can be reused.

Since iodine is the least reactive halogen towards electrophilic substitution, direct iodination of aromatic compounds with iodine presents difficulty and requires strong oxidizing conditions. Thus, a large diversity of methods for synthesis of aromatic iodides have been reported [36]. Some of these reported procedures involved harsh conditions such as nitric acid-sulfuric acid system ($HNO_3/H_2SO4$), iodic acid ($HIO_3$) or periodic acid ($HIO_4/H_2SO_4$), potassium permanganate-sulfuric acid system ($KMnO_4/H_2SO_4$), chromia ($CrO_3$) in acidic solution with iodine, vanadium salts/triflic acid at 100° C., and lead acetate-acetic acid system [$Pb(OAc)_4/HOAc$]. N-iodosuccinimide and triflic acid ($NIS/CF_3SO_3H$) has also been reported for the direct iodination of highly deactivated aromatics. In addition, iodine-mercury(II) halide ($I_2/HgX_2$), iodine monochloride/silver sulfate/sulfuric acid system ($ICl/Ag_2SO_4/H_2SO_4$), N-iodosuccinimide/trifluoroacetic acid ($NIS/CF_3CO_2H$), iodine/silver sulfate ($I_2/Ag_2SO_4$), iodine/1-fluoro-4-chloromethyl-1,4-diazoniabicyclo[2.2.2]octane bis (tetrafluoroborate) ($I_2/F-TEDA-BF_4$), N-iodosuccinimide/acetonitrile ($NIS/CH_2CN$), and ferric nitrate/nitrogen tetroxide [$Fe(NO_2)\ 3/N_2O_4$] are also routinely employed for iodination. Nonetheless, iodination of noscapine even under the most gentle conditions gave only the hydrolysis products, meconine and cotamine [37]. In addition, direct aromatic iodination of noscapine using thallium trifluoroacetate or iodine monochloride also resulted in bond fission between C-5 and C-3' under acidic conditions. Thus, different reaction conditions were tried, based upon varying pH, and found that successful introduction of the iodine atom at the desired C-9 position without disrupting other groups and bonds was stringently dependent on the acidity of the reaction media. A low acidic environment was conducive to effect iodination, whereas, higher acidity was detrimental to the iodination reaction. Thus, in this present work, two different complexes of iodine chloride were used for iodination: pyridine-iodine chloride and potassium iodondichloride. Although the reaction with potassium iodondichloride gave 9-I-nos (5), the yield was low and the desired product was associated with the undesirable hydrolyzed products. A suggestive reason for hydrolysis reaction could be the generation of excess amount of conc. hydrochloric acid in the reagent mixture. Since it was necessary to avoid excess acidity, excess amounts of potassium chloride were employed. Although potassium iodondichloride solutions are most conveniently prepared by the addition of commercial iodine chloride to a solution of potassium chloride, it was possible to modify the procedure of Gleu and Jagemann, wherein, an iodide solution was oxidized with the calculated quantity of iodate in the presence of excess potassium chloride [38]. The pyridine-iodine chloride complex was prepared directly from pyridine and potassium iodondichloride and this procedure avoided the separate isolation of the pyridine-iodine chloride-hydrogen chloride complex [39]. Thus, 9-I-nos (5) was prepared by treating a solution of noscapine in acetonitrile with pyridine-iodine chloride at room temperature for 6 hours followed by raising the temperature to 100° C. for another 6 hours. After cooling, excess ammonia was added and filtered through a celite pad to remove the black nitrogen triiodide. The filtrate was made acidic with 1 M HCl and filtered to collect the yellow solid, washed with water and air-dried to obtain the desired compound in 76% yield. A valuable advantage of this procedure lies in its applicability for the regioselective aromatic iodination of complex natural products.

Conclusions:

Relatively simple and straightforward methods for the direct, and regioselective halogenation of noscapine, which provide halogenated products in high quantitative yields, are provided herein. Although a plethora of reagents and reaction conditions have been reported for aromatic halogenation, most of them did not work well for noscapine, as it is readily hydrolysable. These synthetic strategies effect the desired transformations under mild conditions.

Example 4

Evaluation of Tubulin Binding Properties of Halogenated Noscapine Analogues

Cell Lines and Chemicals:

Cell culture reagents were obtained from Mediatech, Cellgro. CEM, a human lymphoblastoid line was provided by Dr. William T. Beck (Cancer Center, University of Illinois at Chicago). MCF-7 cells were maintained in Dulbecco's Modification of Eagle's Medium 1× (DMEM) with 4.5 g/L glucose and L-glutamine (Mediatech, Cellgro) supplemented with 10% fetal bovine serum (Invitrogen, Carlsbad, Calif.) and 1% penicillin/streptomycin (Mediatech, Cellgro). MDA-MB-231 and CEM cells were grown in RPMI-1640 medium supplemented with 10% fetal bovine serum, and 1% penicillin/streptomycin. Mammalian brain microtubule proteins were isolated by two cycles of polymerization and depolymerization and tubulin was separated from the microtubule binding proteins by phosphocellulose chromatography. The tubulin solution was stored at −80° C. until use.

In Vitro Cell Proliferation Assays

Sulforhodamine B (SRB) assay: The cell proliferation assay was performed in 96-well plates as described previously [12,28]. Adherent cells (MCF-7 and MDA-MB-231) were seeded in 96-well plates at a density of $5\times10^3$ cells per well. They were treated with increasing concentrations of the halogenated analogs the next day while in log-phase growth. After 72 hours of drug treatment, cells were fixed with 50% trichloroacetic acid and stained with 0.4% sulforhodamine B dissolved in 1% acetic acid. After 30 minutes, cells were then washed with 1% acetic acid to remove the unbound dye. The protein-bound dye was extracted with 10 mM Tris base to determine the optical density at 564-nm wavelength.

MTS Assay:

Suspension cells (CEM) were seeded into 96-well plates at a density of $5\times10^3$ cells per well and were treated with increasing concentrations of all halogenated analogs for 72 hours. Measurement of cell proliferation was performed colorimetrically by 3-(4,5-dimethylthiazol-2-yl)-5-(3-carboxymethoxyphenyl)-2-(4-sulphophenyl)-2H-tetrazolium, inner salt (MTS) assay, using the CellTiter96 AQueous One Solution Reagent (Promega, Madison, Wis.). Cells were exposed to MTS for 3 hours and absorbance was measured using a microplate reader (Molecular Devices, Sunnyvale, Calif.) at an optical density (OD) of 490 nm. The percentage of cell survival as a function of drug concentration for both the assays was then plotted to determine the $IC_{50}$ value, which stands for the drug concentration needed to prevent cell proliferation by 50%.

4'-6-diamidino-2-phenylindole (DAPI) staining

Cell morphology was evaluated by fluorescence microscopy following DAPI staining (Vectashield, Vector Labs, Inc., Burlingame, Calif.). MDA-MB-231 cells were grown on poly-L-lysine coated coverslips in 6-well plates and were treated with the halogenated analogs at 25 µM for 72 hours. After incubation, coverslips were fixed in cold methanol and washed with PBS, stained with DAPI, and mounted on slides. Images were captured using a BX60 microscope (Olympus, Tokyo, Japan) with an 8-bit camera (Dage-MTI, Michigan City, Ind.) and IP Lab software (Scanalytics, Fairfax, Va.). Apoptotic cells were identified by features characteristic of apoptosis (e.g. nuclear condensation, formation of membrane blebs and apoptotic bodies).

Tubulin Binding Assay:

Fluorescence titration for determining the tubulin binding parameters was performed as described previously [29]. In brief, 9-F-nos, 9-Cl-nos, 9-Br-nos or 9-I-nos (0-100 µM) was incubated with 2 µM tubulin in 25 mM PIPES, pH 6.8, 3 mM $MgSO_4$, and 1 mM EGTA for 45 min at 37° C. The relative intrinsic fluorescence intensity of tubulin was then monitored in a JASCO FP-6500 spectrofluorometer (JASCO, Tokyo, Japan) using a cuvette of 0.3-cm path length, and the excitation wavelength was 295 nm. The fluorescence emission intensity of noscapine and its derivatives at this excitation wavelength was negligible. A 0.3-cm path-length cuvette was used to minimize the inner filter effects caused by the absorbance of these agents at higher concentration ranges. In addition, the inner filter effects were corrected using a formula F corrected=F observe·antilog [(Aex+Aem)/2], where Aex is the absorbance at the excitation wavelength and Aem is the absorbance at the emission wavelength. The dissociation constant (Kd) was determined by the formula: 1/B=Kd/[free ligand]+1, where B is the fractional occupancy and [free ligand] is the concentration of 9-F-nos, 9-Cl-nos, 9-Br-nos or 9-I-nos. The fractional occupancy (B) was determined by the formula B=ΔF/ΔFmax, where ΔF is the change in fluorescence intensity when tubulin and its ligand are in equilibrium and ΔFmax is the value of maximum fluorescence change when tubulin is completely bound with its ligand. ΔFmax was calculated by plotting 1/ΔF versus 1/[free ligand].

Cell Cycle Analysis:

The flow cytometric evaluation of the cell cycle status was performed as described previously [12]. Briefly, $2\times10^6$ cells were centrifuged, washed twice with ice-cold PBS, and fixed in 70% ethanol. Tubes containing the cell pellets were stored at 4° C. for at least 24 hours. Cells were then centrifuged at 1000×g for 10 min and the supernatant was discarded. The pellets were washed twice with 5 ml of PBS and then stained with 0.5 ml of propidium iodide (0.1% in 0.6% Triton-X in PBS) and 0.5 ml of RNase A (2 mg/ml) for 45 minutes in dark. Samples were then analyzed on a FACSCalibur flow cytometer (Beckman Coulter Inc., Fullerton, Calif.).

Immunofluorescence Microscopy:

Cells adhered to poly-L-lysine coated coverslips were treated with noscapine and its halogenated analogs (9-F-nos, 9-Cl-nos, 9-Br-nos, 9-I-nos for 0, 12, 24, 48 and 72 hours. After treatment, cells were fixed with cold (−20° C.) methanol for 5 min and then washed with phosphate-buffered saline (PBS) for 5 min. Non-specific sites were blocked by incubating with 100 µl of 2% BSA in PBS at 37° C. for 15 min. A mouse monoclonal antibody against α-tubulin (DM1A, Sigma) was diluted 1:500 in 2% BSA/PBS (100 µl) and incubated with the coverslips for 2 hours at 37° C. Cells were then washed with 2% BSA/PBS for 10 min at room temperature before incubating with a 1:200 dilution of a fluorescein-isothiocyanate (FITC)-labeled goat anti-mouse IgG antibody (Jackson ImmunoResearch, Inc., West Grove, Pa.) at 37° C. for 1 hour. Coverslips were then rinsed with 2% BSA/PBS for 10 min and incubated with propidium iodide (0.5 µg/ml) for 15 min at room temperature before they were mounted with Aquamount (Lerner Laboratories, Pittsburgh, Pa.) containing 0.01% 1,4-diazobicyclo(2,2,2)octane (DABCO, Sigma). Cells were then examined using confocal microscopy for microtubule morphology and DNA fragmentation (at least 100 cells were examined per condition). Propidium iodide staining of the nuclei was used to visualize the multinucleated and micronucleated DNA in this study.

Results and Discussion

Figure 5:
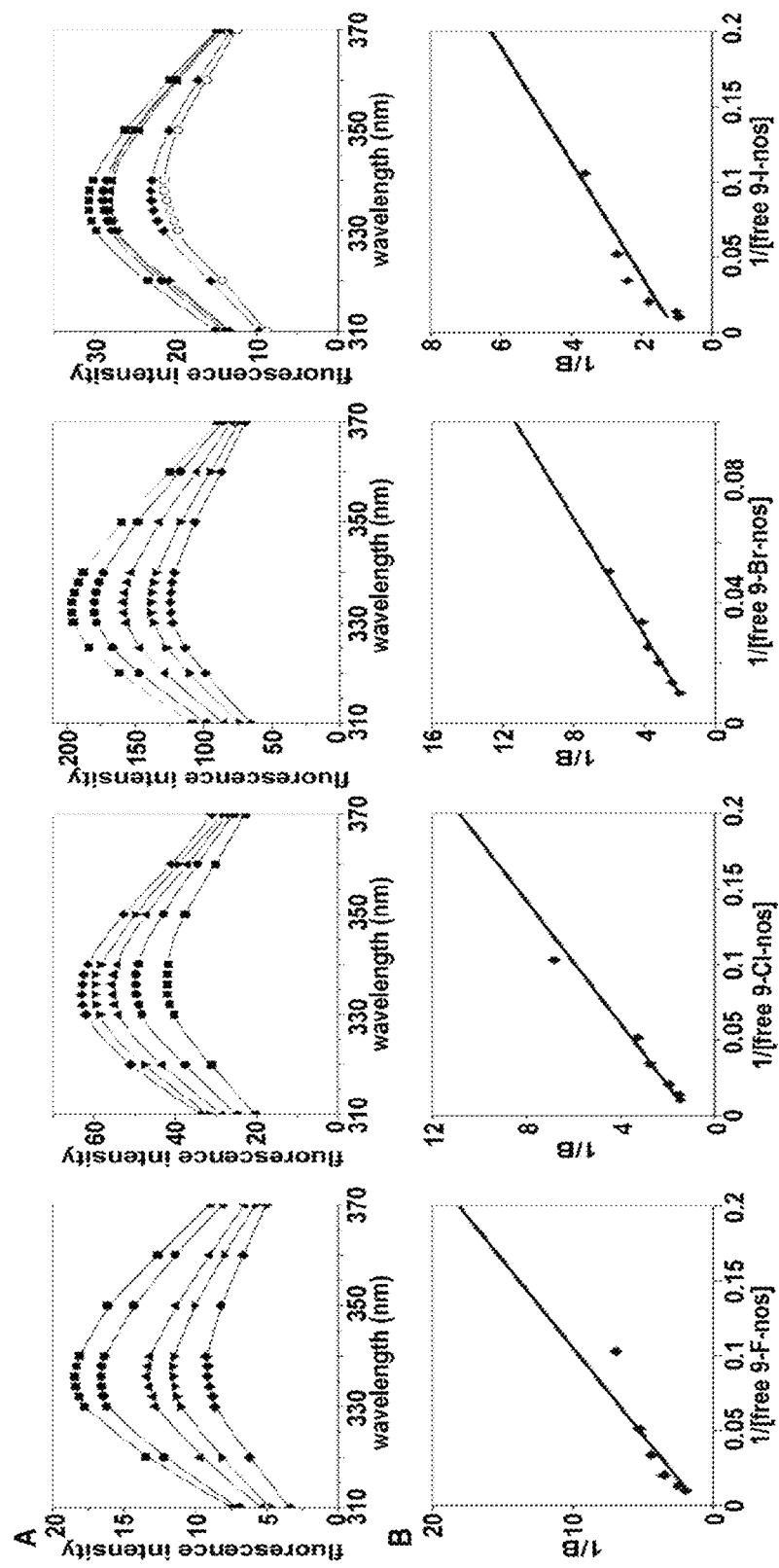
FIGS. 5A and 5B are charts showing the fluorescence quenching of tubulin by halogenated derivatives of noscapine, namely, 9-F-nos, 9-Cl-nos, 9-Br-nos and 9-I-nos.

Halogenated Noscapine Analogs have Higher Tubulin Binding Activity than Noscapine One aspect of the analysis of the anti-tumor properties of the compounds involved determining whether the halogenated noscapine analogs bind tubulin like the parent compound, noscapine. Tubulin, like many other proteins, contains fluorescent amino acids like tryptophans and tyrosines and the intensity of the fluorescence emission is dependent upon the micro-environment around these amino acids in the folded protein. Agents that bind tubulin typically change the micro-environment and the fluorescent properties of the target protein [18,40,41]. Measuring these fluorescent changes has become a standard method for determining the binding properties of tubulin ligands including the classical compound colchicine [42]. This standard method was used to determine the dissociation constant (Kd) between tubulin and the halogenated analogs (9-F-nos, 9-Cl-nos, 9-Br-nos, and 9-I-nos). The data showed that all halogenated noscapine analogs quenched tubulin fluorescence in a concentration-dependent manner (FIG. 5A, upper panels). The dissociation constant for noscapine binding to tubulin (Kd) is 144±2.8 µM [18], 54±9.1 µM for 9-Br-nos [12] binding to tubulin and 40±804 for 9-Cl-nos [43] binding to tubulin. The double reciprocal plots yielded a dissociation constant (Kd) of 81±8 µM for 9-F-nos, and 22±404 for 5-I-nos, binding to tubulin. These results thus indicate that all halogenated analogs bind to tubulin with a greater affinity than noscapine in the following order of magnitude: 9-I-nos>9-Cl-nos>9-Br-nos>9-F-nos>Nos.

Effects of Halogenated Noscapine Analogs on Proliferation of Cancer Cells

Having identified tubulin as the target molecule, the pharmacological study was extended at the cellular level to determine if all the halogenated analogs affected cancer cell proliferation. As a preliminary screen, all compounds including the parent noscapine were evaluated for their antiproliferative activity in three human cancer cell lines; human breast adenocarcinoma cells (estrogen- and progesterone-receptor positive, MCF-7 and estrogen- and progesterone-receptor negative, MDA-MB-231) and human lymphoblastoid cells CEM. The test compounds were dissolved in DMSO to provide a concentration range of 10 nm to 1000 µM. Sulforhodamine B (SRB) was used in an in vitro proliferation assay to determine the $IC_{50}$ values that stand for the drug concentration required to achieve a cell kill of 50%. The $IC_{50}$ values for all the halogenated analogs for these three cell lines are collated in Table 2.

9-I-nos was found to possess modest cytotoxic effects and in sharp contrast, 9-F-nos, 9-Cl-nos and 9-Br-nos exhibited potent cytotoxic activity. The $IC_{50}$ value amounted to 1.9±0.3 04 and 1.0±0.2 µM with 9-Cl-nos and 9-Br-nos, respectively, for MCF-7 cells, which reflects a pronounced antiproliferative activity. Surprisingly, 9-Br-nos showed a ~40 fold higher cytotoxic activity ($IC_{50}$=1.0±0.2 µM) than noscapine ($IC_{50}$=39.6±2.2 µM). Parenthetically, it is worth mentioning that a similar low $IC_{50}$ value of 1.2±0.3 04 and 1.9±0.2 µM was measured using 9-Cl-nos and 9-Br-nos, respectively, for the CEM cells. Interestingly, the $IC_{50}$ values of 1.9±0.3 µM and 3.5±0.4 µM with 9-Cl-nos for MDA-MB-231 and MCF-7 cells, respectively, are close suggesting that 9-Cl-nos inhibits cellular proliferation of cancer cells independent of hormone receptor status. Thus this preliminary screen with the three chosen cell lines revealed 9-F-nos, 9-Cl-nos, 9-Br-nos as potent cytotoxic compounds exemplified by their much lower $IC_{50}$ values as compared to noscapine. The iodo-substituent at position-9 resulted in improved cytotoxic activity than the parent noscapine in some cell types, such as MDA-MB-231, but not better than noscapine in other cell types, such as CEM.

Although a definitive correlation of the sensitivity of cancer cells to these analogs cannot yet be established at this stage, it is evident that tubulin represents a potential target for these compounds. The results suggest that the $IC_{50}$ values do not show a correlation among these analogs and are cell-type dependent.

Figure 6:
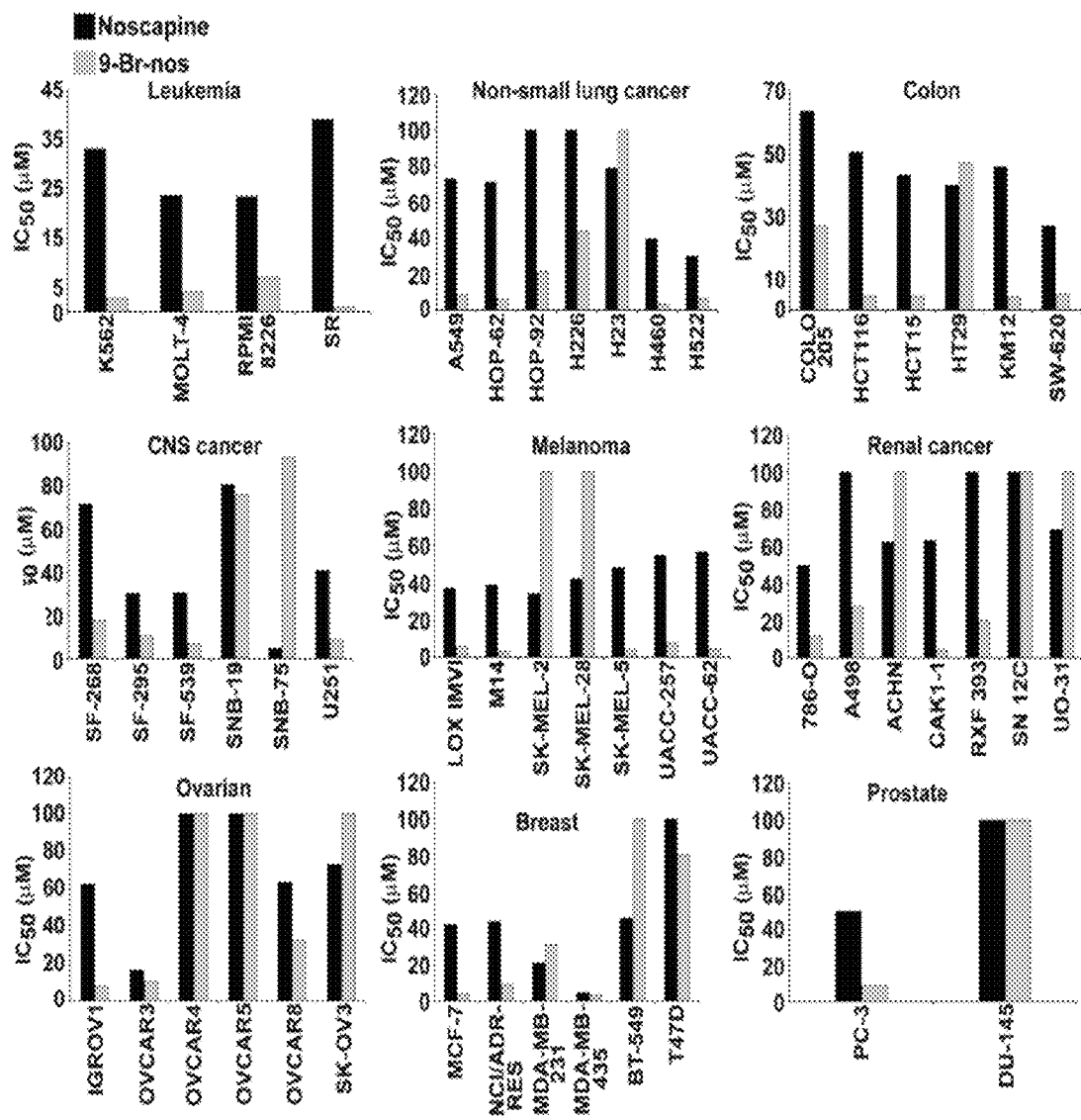
FIG. 6 is a series of charts showing that 9-Br-nos is much more active than noscapine in inhibiting the proliferation of various human cancer cells, based on an analysis of the National Cancer Institute's (NCI's) panel of 60 cancer cell lines. The panel of 60 human tumor cell lines is organized into subpanels representing leukemia, non-small cell lung, colon, CNS, melanoma, renal, ovarian, breast and prostrate cancer lines. Cells were treated with noscapine and 9-Br-nos at increasing gradient concentrations for 48 hours. The $IC_{50}$ values, which stand for the drug concentration needed to prevent cell proliferation by 50% was then measured using an in vitro Sulforhodamine B assay. Panels show bar-graphically the comparison of $IC_{50}$ values of noscapine (black bars) and 9-Br-nos (grey bars) for cancer cell lines of various tissue origins.

The effectiveness of 9-F-nos was demonstrated against NCI's panel of 60 human cancer cell lines, with the data shown in FIG. 6. The panel of 60 human tumor cell lines is organized into subpanels representing leukemia, non-small cell lung, colon, central nervous system (CNS), melanoma, renal, ovarian, breast and prostrate cancer lines. FIG. 6 shows a bar-graphical representation depicting a comparison of the $IC_{50}$ values of both noscapine and 9-Br-nos for the NCI 60 tumor cell line panel.

Figure 7:
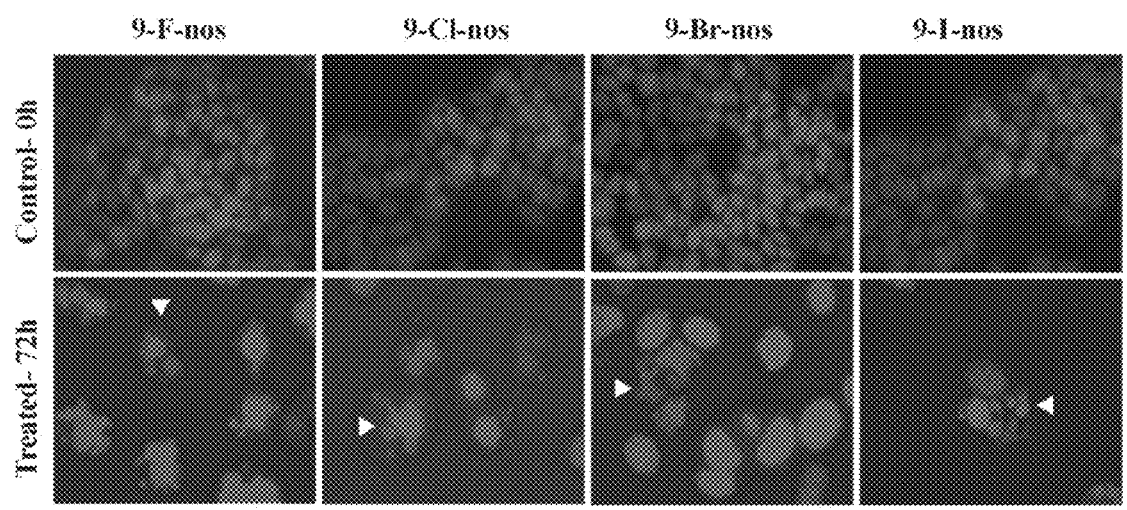
FIG. 7 is a series of photographs showing the effect of various halogenated noscapine analogues on the morphology of cancer cells. Morphologic criteria for apoptotic cell death include, for example, chromatin condensation with aggregation along the nuclear envelope and plasma membrane blebbing followed by separation into small, apoptotic bodies. Panels show morphological evaluation of nuclei stained with DAPI from control cells (upper panels) and cells treated with 25 µM concentration of 9-F-nos, 9-Cl-nos, 9-Br-nos, and 9-I-nos for 72 hours (lower panels) using fluorescence microscopy. Several typical features of apoptotic cells such as condensed chromosomes, numerous fragmented micronuclei, and apoptotic bodies are evident (indicated by white arrowheads) upon 72 hours of drug treatment. (Scale bar=15 µm)

Besides the antiproliferative effect, morphological evaluation using DAPI staining revealed condensed chromatin along with numerous fragmented nuclei (shown by white arrowheads), indicative of apoptotic cell death (FIG. 7), that was investigated next.

Halogenated Noscapine Analogs Alter the Cell Cycle Profile and Cause Mitotic Arrest at G2/M Phase More Actively than Noscapine.

Figures 1, 8:
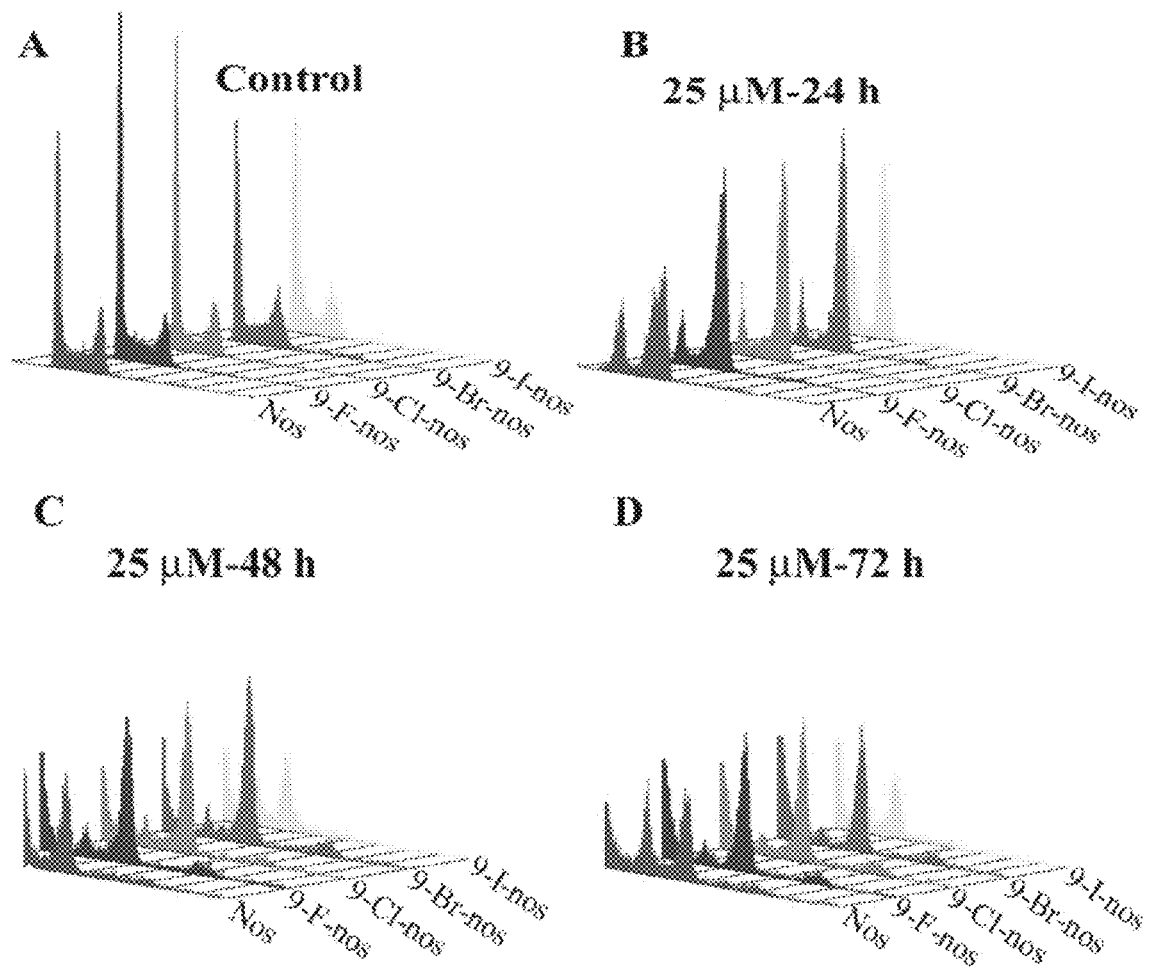
FIGS. 8 A-D depict analyses of cell cycle distribution in a three-dimensional disposition as determined by flow cytometry in MCF-7 cells treated with 25 µM concentration of all 5 compounds (Nos, 9-F-nos, 9-Cl-nos, 9-Br-nos and 9-I-nos) for 0, 24, 48 and 72 hours respectively.
Figures 2, 8:
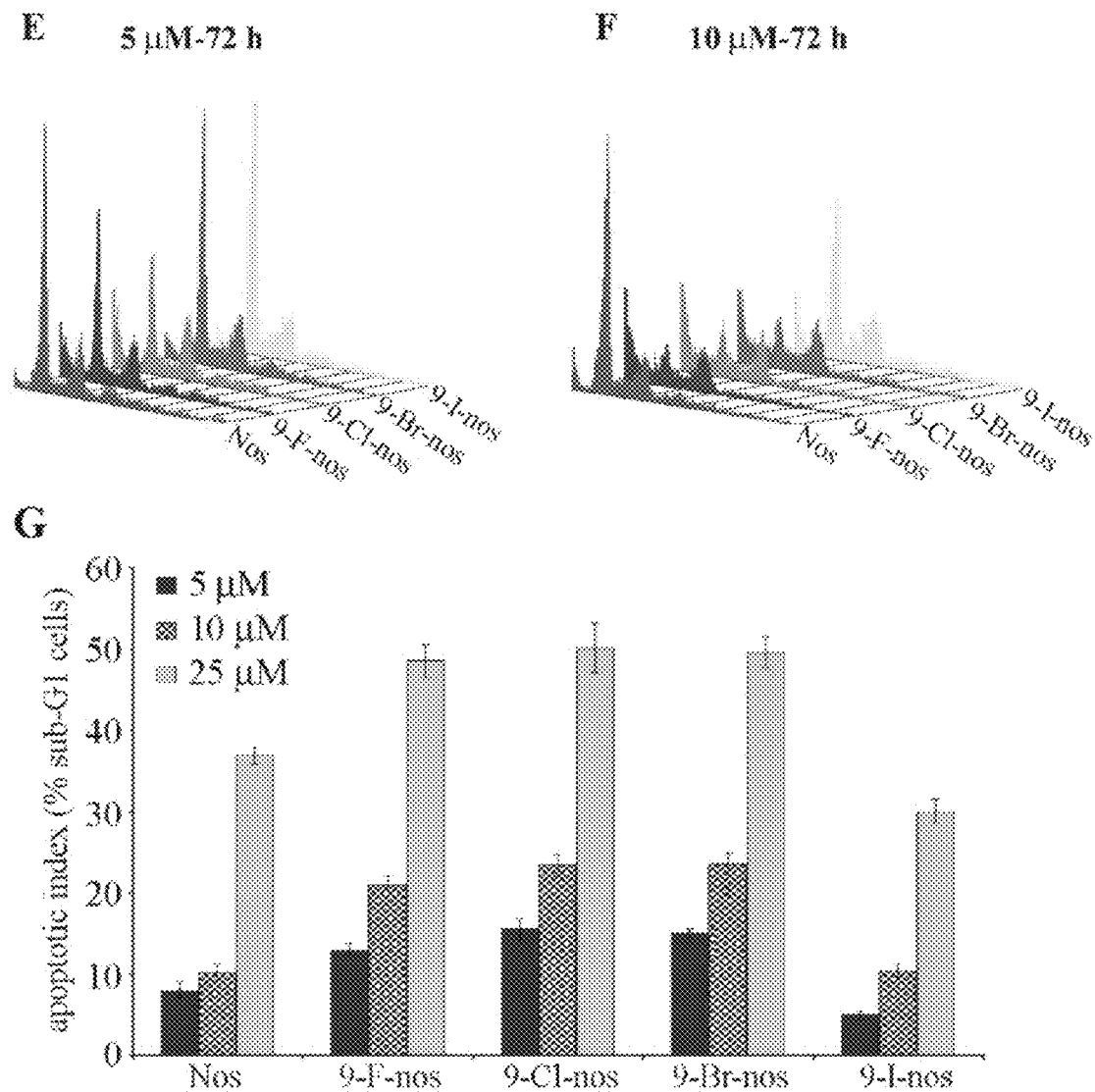

To investigate the precise mechanisms of cell death, the effect of halogenated analogs on percent G2/M cells (mitotic index) and percent sub-G1 cells (apoptotic index) was examined as a function of dose and time in MCF-7 cells using fluorescence activated cell sorting (FACS) analysis. The effect of all compounds including noscapine was evaluated at three doses-5 µM, 10 µM and 25 µM for 0, 24, 48 and 72 hours of drug treatment. FIG. 8 (FIGS. 8 A-F) shows the cell cycle profile in a three-dimensional disposition for all the compounds included in the course of this study. Fluorescently labeled DNA is a good indicator of cell cycle progression and cell death. An unreplicated complement of diploid (2N) DNA cells represents the G1 phase while duplicated tetraploid (4N) DNA cells represent G2 and M phases. Cells in the process of DNA duplication between diploid and tetraploid peaks represent S phase when DNA is being synthesized. Less than diploid DNA appears in populations of dying cells that degrade their DNA to different extents. Treatment of MCF-7 cells with these compounds for 0, 24, 48 and 72 hours led to profound perturbations of the cell cycle profile at 25 µM (FIGS. 8 A-D). The results show that 9-F-nos, 9-Cl-nos and 9-Br-nos induced a massive accumulation of cells in the G2/M phase at 24 hours. For example, the G2/M cell population increased from 18.5% in the control to ~66% in MCF-7 cells treated with 25 µM 9-F-nos for 24 hours. The distribution of cell population over G0/G1, S, G2/M and sub-G1 phases of the cell cycle for 25 µM concentration is shown in Table 3.

TABLE 3

Effect of halogenated derivatives of noscapine on cell cycle progression of MCF-7 cells

| Cell Cycle parameters % | 0 h | | | | 24 h | | | |
|---|---|---|---|---|---|---|---|---|
| | Sub-$G_1$ | $G_0/G_1$ | S | $G_2/M$ | Sub-$G_1$ | $G_0/G_1$ | S | $G_2/M$ |
| Nos | 0.2 ± 0.03 | 54.8 ± 0.03 | 13.2 ± 0.2 | 29.9 ± 2.2 | 10.2 ± 1.2 | 18.3 ± 3.3 | 3.4 ± 0.8 | 50.2 ± 3.6 |
| 9-F-nos | 0.2 ± 0.04 | 67.7 ± 5.6 | 11.9 ± 1.5 | 18.5 ± 2.2 | 6.8 ± 2.1 | 10.8 ± 2.4 | 3.8 ± 1.1 | 65.9 ± 4.4 |
| 9-Cl-nos | 1.4 ± 0.5 | 69 ± 5.6 | 7.5 ± 1.6 | 20.7 ± 3.4 | 15.3 ± 2.5 | 11.5 ± 2.7 | 4.3 ± 1.4 | 59.7 ± 5.2 |
| 9-Br-nos | 0.2 ± 0.1 | 53.3 ± 2.8 | 12.7 ± 1.8 | 28.9 ± 4.4 | 6.9 ± 2.4 | 10.4 ± 1.8 | 3.4 ± 1.2 | 61.9 ± 3.6 |
| 9-I-nos | 0.3 ± 0.2 | 60.6 ± 4.6 | 13.9 ± 2.3 | 23.1 ± 3.7 | 7.7 ± 1.7 | 17 ± 2.3 | 3.1 ± 1.3 | 44.5 ± 5.1 |

| Cell Cycle parameters % | 48 h | | | | 72 h | | | |
|---|---|---|---|---|---|---|---|---|
| | Sub-$G_1$ | $G_0/G_1$ | S | $G_2/M$ | Sub-$G_1$ | $G_0/G_1$ | S | $G_2/M$ |
| Nos | 36.8 ± 3.7 | 19.8 ± 1.9 | 4.1 ± 0.6 | 28.07 ± 0.2 | 36.9 ± 0.2 | 20.5 ± 0.2 | 7.06 ± 0.2 | 26.3 ± 0.2 |
| 9-F-nos | 34.5 ± 2.5 | 7.9 ± 2.8 | 3.5 ± 0.8 | 43.7 ± 2.9 | 48.6 ± 3.3 | 5.2 ± 2.2 | 3.6 ± 1.5 | 34.4 ± 3.4 |
| 9-Cl-nos | 37.8 ± 3.2 | 8 ± 3.3 | 4 ± 1.1 | 42.4 ± 3.8 | 50.2 ± 2.5 | 5.9 ± 1.9 | 4.1 ± 1.4 | 35.3 ± 3.9 |
| 9-Br-nos | 35.1 ± 3.5 | 6.5 ± 2.5 | 2.8 ± 0.7 | 43.8 ± 3.4 | 49.6 ± 2.7 | 4.6 ± 2.1 | 2.4 ± 1.6 | 33.7 ± 3.5 |
| 9-I-nos | 28.1 ± 3.1 | 15.4 ± 4.5 | 2.9 ± 0.6 | 25.9 ± 4.1 | 30.1 ± 3.1 | 17 ± 1.9 | 4.9 ± 2.2 | 20.7 ± 2.2 |

MCF-7 cells were treated with 25 μM solution for the indicated time (h) before being stained with propidium iodide (PI) for cell cycle analysis. Values represent mean ± S.E.M.

More subtle effects that helped us to determine the sensitivity of MCF-7 cells to halogenated analogs for induction of mitotic block were evident at lower dose regimes i.e. 5 and 10 μM. Panels E and F (FIG. 8) show the three-dimensional cell cycle profile of MCF-7 cells treated for 72 hours with 5 μM and 10 μM, respectively, □ for all the five compounds. In parallel to the G2/M block, a characteristic hypodiploid DNA content peak (sub-G1) is seen to be rising at 48 and 72 hours of drug treatment for all the three doses studied. The progressive generation of cells having hypodiploid DNA content indicates apoptotic cells with fragmented DNA. The percent sub-G1 population for the three doses (5 μM, 10 μM, and 25 μM) has been plotted for all the compounds in FIG. 4, Panel G. It is evident from the bar-graphical representation that a 72 hour treatment at 25 μM for MCF-7 cells, the percentage of sub-G1 cells is almost similar for 9-F-nos, 9-Cl-nos and 9-Br-nos. However, the sub-G1 population is slightly lower for 9-I-nos than noscapine at 25 μM. At lower doses, the percent sub-G1 cells were higher for 9-F-nos, 9-Cl-nos and 9-Br-nos than the parent compound noscapine. Thus, the data show differences at 5 μM and 10 μM concentrations of the halogenated compounds in the extent of their deleterious effect on the cell cycle by an increase in the percentage of sub-G1 cells having hypodiploid DNA content, characteristic of apoptosis.

Figure 9:
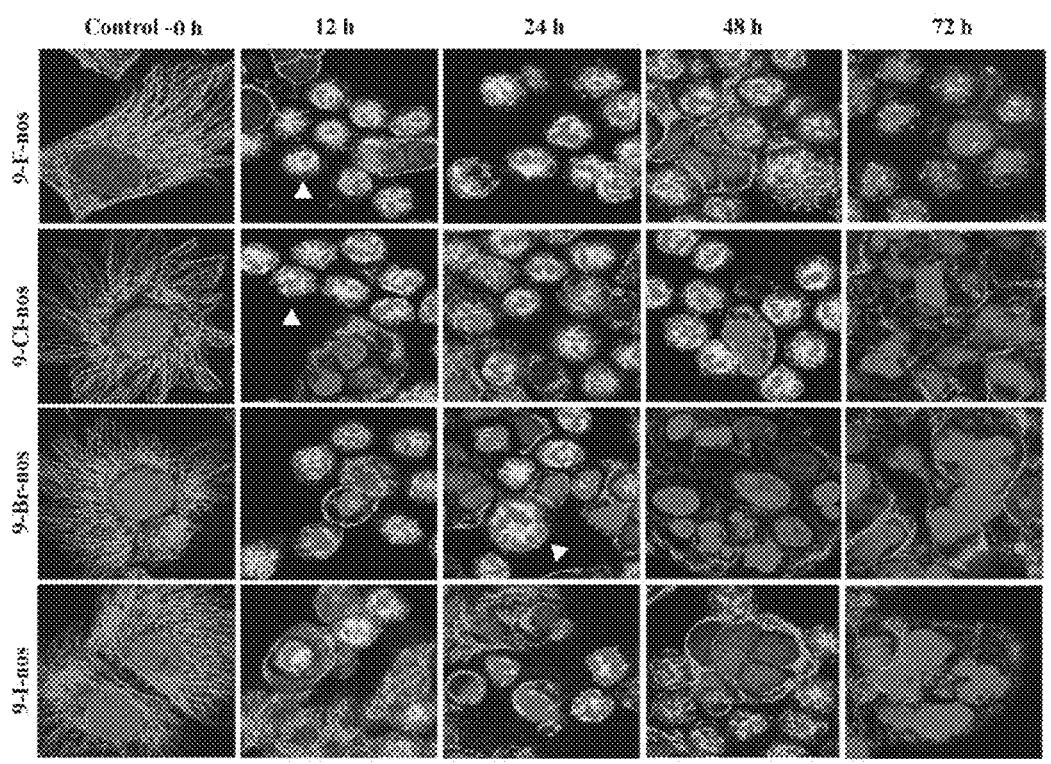
FIG. 9 is a series of immunofluorescence confocal micrographs showing that halogenated noscapine analogs induce spindle abnormalities. The immunofluorescence confocal micrographs are of MCF-7 cells treated for 0, 12, 24, 48 and 72 hours with 25 µM concentration of all 5 compounds (Nos, 9-F-nos, 9-Cl-nos, 9-Br-nos and 9-I-nos). Mitotic figures are abundant at 24 hours, while apoptotic figures start to appear at 48 hours. (Scale bar=30 µm)

Effect of Halogenated Noscapine Analogs on Spindle Architecture and Nuclear Morphology To test whether these halogenated noscapine analogs induce spindle abnormalities prior to apoptotic cell death indicated by nuclear fragmentation of dying cells, the spindle architecture and nuclear morphology of MCF-7 cells treated with the halogenated analogs was evaluated using confocal microscopy (FIG. 9). MCF-7 cells were treated with 25 μM 9-F-nos, 9-Cl-nos, 9-Br-nos and 9-I-nos for 0, 12, 24, 48 and 72 hours. It was found that while untreated MCF-7 cells exhibited normal radial microtubule arrays in normal interphase cells, treated cells exhibited pronounced spindles and condensed chromosomes that are not organized at the metaphase plate indicating mitotic arrest commencing as early as 12 hours, and maximizing at 24 hours of drug treatment, when numerous mitotically arrested cells were visible (indicated by white arrowheads, FIG. 9). While not wishing to be bound to a particular theory, this was probably due to the activation of the spindle assembly checkpoint, a cellular surveillance mechanism that monitors the integrity of the mitotic spindle [20]. After 48 hours of treatment, the population of arrested cells decreased and micronucleated and multinucleated cells were observed (white arrowheads, FIG. 9, 9-Br-nos, 48 hours). The immunofluorescence experiments correlated well with our cell cycle progression experiments that offered comparable results at similar time regimens and displayed DNA degradation (sub-G1 population) at 48 and 72 hours of treatment.

Conclusions

Most importantly, the results show that halogenation of noscapine increases its tubulin-binding activity and impacts its therapeutic potential for a variety of cancer cell types. Furthermore, the mechanism of apoptotic cell death caused by these halogenated analogs is preserved, in that, like noscapine, cell death is preceded by extensive mitotic arrest. Taken together, like noscapine, these analogs indicate a great potential for further preclinical and clinical evaluation.

REFERENCES

1. Mitchison T J, Kirschner M. Dynamic instability of microtubule growth. Nature 1984; 312:237-242.
2. Kirschner M, Mitchison T J. Beyond self-assembly: From microtubules to morphogenesis. Cell 1986; 45:329-342.
3. McIntosh J R. The role of microtubules in chromosome movement, in Microtubules 1994 (Hyams J S and Lloyd C W eds) pp 413-434, Wiley-Liss, New York.
4. Jordan M A, Wilson L. Microtubules as a target for anticancer drugs. Nat Rev Cancer 2004; 4:253-265.
5. Zhou J, Giannakakou P. Targeting microtubules for cancer chemotherapy. Curr Med Chem Anticancer Agents 2005; 5:65-71.
6. van Tellingen O, Sips J H, Beijnen J H, Bult A, Nooijen W J. Pharmacology, bio-analysis and pharmacokinetics of the vinca alkaloids and semi-synthetic derivatives. Anticancer Res 1992; 12:1699-1715.
7. Rowinsky E K. The development and clinical utility of the taxane class of antimicrotubule chemotherapy agents. Ann Rev. Med. 1997; 48:353-374.
8. Crown J, O'Leary M. The taxanes: an update. Lancet 2000; 355:1176-1178.
9. Anderson J T, Ting A E, Boozer S, Brunden K R, Crumrine C, Danzig J, Dent, T. Faga L, Harrington J J, Hodnick W F, Murphy S M, Pawlowski G, Perry R, Raber A, Rundlett S E, Stricker-Krongrad A, Wang J, Bennani Y L. Identification of novel and improved antimitotic agents derived from noscapine. J. Med. Chem. 2005; 48:7096-8.
10. Anderson J T, Ting A E, Boozer S, Brunden K R, Danzig J, Dent T, Harrington J J, Murphy S M, Perry R, Raber A, Rundlett S E, Wang J, Wang N, Bennani Y L. Discovery of S-phase arresting agents derived from noscapine. J Med Chem 2005; 48:2756-2758.
11. Aneja R, Zhou J, Vangapandu S N, Zhou B, Chandra R, Joshi H C. Drug resistant T-lymphoid tumors apoptose selectively by an antimicrotubule agent, EM011. Blood 2006 (In Press, prepublished online Nov. 10, 2005).
12. Zhou J, Gupta K, Aggarwal S, Aneja R, Chandra R, Panda D, Joshi H C. Brominated derivatives of noscapine are potent microtubule-interfering agents that perturb mitosis and inhibit cell proliferation. Mol Pharmacol 2003; 63:799-807.
13. Zhou J, Liu M, Aneja R, Chandra R, Joshi H C. Enhancement of paclitaxel-induced microtubule stabilization, mitotic arrest, and apoptosis by the microtubule-targeting agent EM012. Biochem Pharmacol 2004; 68:2435-2441.
14. Zhou J, Liu M, Luthra R, Jones J, Aneja R, Chandra R, Tekmal R R, Joshi H C. EM012, A microtubule-interfering agent, inhibits the progression of multidrug-resistant human ovarian cancer both in cultured cells and in athymic nude mice. Cancer Chemother Pharmacol 2005; 55:461-465.
15. Checchi P M, Nettles J H, Zhou J, Snyder J P, Joshi H C. Microtubule-Interacting Drugs for Cancer Treatment. Trends Pharmacol Sci 2003; 24:361-365.
16. Joshi H C, Zhou J. Noscapine and Analogues as Potential Chemotherapeutic Agents. Drug News Perspect 2000; 13:543-546.
17. Seetharaman J, Rajan S S. Crystal and Molecular Structure of Noscapine. Zeftschrm fur Kristamographic 1995; 210:111-113.
18. Ye K, Ke Y, Keshava N, Shanks J, Kapp J A, Tekmal R R, Petros J, Joshi H C. Opium alkaloid noscapine is an antitumor agent that arrests metaphase and induces apoptosis in dividing cells. Proc Natl Acad Sci USA 1998; 95:1601-1606.
19. Ye K, Zhou J, Landen J W, Bradbury E M, Joshi H C. Sustained Activation of p34(cdc2) is Required for Noscapine-Induced Apoptosis. J Biol Chem 2001; 276:46697-46700.
20. Zhou J, Panda D, Landen J W, Wilson L, Joshi H C. Minor alteration of microtubule dynamics causes loss of tension across kinetochore pairs and activates the spindle checkpoint. J Biol Chem 2002; 277:17200-17208.
21. Zhou J, Gupta K, Yao J, Ye K, Panda D, Giannakakou P, Joshi H C. Paclitaxel-resistant human ovarian cancer cells undergo c-Jun NH2-terminal kinase-mediated apoptosis in response to noscapine. J Biol Chem 2002; 277:39777-39785.
22. Ke Y, Ye K, Grossniklaus H E, Archer D R, Joshi H C, Kapp J A. Noscapine inhibits tumor growth with little toxicity to normal tissues or inhibition of immune Responses., Cancer Immunol Immunother 2000; 49:217-225.
23. Landen J W, Lang R, McMahon S J, Rusan N M, Yvon A M, Adams A W, Sorcinelli M D, Campbell R, Bonaccorsi P, Ansel J C, Archer D R, Wadsworth P, Armstrong C A, Joshi H C. Noscapine alters microtubule dynamics in living cells and inhibits the progression of melanoma. Cancer Res 2002; 62:4109-4114.
24. Landen J W, Hau V, Wang M S, Davis T, Ciliax B, Wainer B H, Van Meir E G, Glass J D, Joshi H C, Archer D R. Noscapine Crosses the Blood-brain Barrier and Inhibits Glioblastoma Growth. Clin Cancer Res 2004; 10:5187-5201.
25. Dahlstrom B, Mellstrand T, Lofdahl C Johansson M. Pharmacokinetic properties of noscapine. Eur J Clin Pharmacol 1982; 22:535-539.
26. Segal M S, Goldstein M M, Attinger E O. The Use of Noscapine (Narcotine) as an Antitussive Agent. Dis Chest 1957; 32:305-309.
27. Loder R E. Safe Reduction of the Cough Reflex with Noscapine: A Preliminary Communication on a New Use for an Old Drug. Anaesthesia 1969; 24:355-358.
28. Skehan P, Storeng R, Scudiero D, Monks A, McMahon J, Vistica D, Warren J T, Bokesch H, Kenney S, Boyd M R. New colorimetric cytotoxicity assay for anticancer-drug screening. J Natl Cancer Inst 1990; 82:1107-1112.
29. Joshi H C, Zhou J. Gamma tubulin and microtubule nucleation in mammalian cells. Methods Cell Biol 2001; 67:179-193.
30. Schmid H. Bromination with Bromosuccinimide in the Presence of Catalysts. II. Hely Chim Acta 1946; 29:1144-1151.
31. Lambert F L, Ellis W D, Parry R J. Halogenation of Aromatic Compounds by N-Bromo- and N-Chlorosuccinimide under Ionic Conditions. J Org Chem 1965; 30:304-306.
32. Dey B B, Srinivasan T K. Cotamine Series. IV. 5-Bromonarcotine, 5-Bromocotarnine, 5-Bromohydrocotarnine and 5-Bromonarceine and Their Derivatives. J Indian Chem Soc 1935; 12:526-536.
33. Cainelli G, Manescalchi F. Polymer-Supported Reagents. The Use of Anion-Exchange Resins in the Synthesis of Primary and Secondary Alkyl Fluorides from Alkyl Halides or Alkyl Methanesulfonates. Synthesis 1976; 472-473.
34. Tanemura K, Suzuki T, Nishida Y, Satsumabayashi K, Horaguchi T. Halogenation of Aromatic Compounds by N-chloro-, N-bromo- and N-iodosuccinimide. Chem Lett 2003; 32:932-933.
35. Stokker G E, Deana A A, deSolms S J, Schultz E M, Smith R L, Cragoe E J Jr, Baer J E, Ludden C T, Russo H F, Scriabine A, Sweet C S, Watson L S. 2-(Aminomethyl) phenols, a New Class of Saluretic Agents. 1. Effects of Nuclear Substitution. Med Chem 1980; 23:1414-1427.
36. Hajipour A R, Arbabian M, Ruoho A E. Tetramethylammonium Dichloroiodate: An Efficient and Environmentally Friendly Iodination Reagent for Iodination of Aromatic Compounds under Mild and Solvent-Free Conditions. J Org Chem 2002; 67:8622-8624.
37. Lee D U. (−)-β-Narcotine: a facile synthesis and the degradation with ethyl chloroformate. Bull Korean Chem Soc 2002; 23:1548-1552.
38. Gleu K, Jagemann W. Action of Iodine Monochloride upon Heterocyclic Bases. J Prakt Chem 1936; 145:257-264.
39. Firouzabadi H, Iranpoor N, Shiri M. Direct and Regioselective Iodination and Bromination of Benzene, Naphthalene and Other Activated Aromatic Compounds Using Iodine and Bromine or Their Sodium Salts in the Presence of the Fe(NO3)3.1.5$N_2O_4$/Charcoal System. Tetrahedron Lett 2003; 44:8781-8785.
40. Peyrot V, Leynadier D, Sarrazin M, Briand C, Menendez M, Laynez J, Andreu J M. Mechanism of binding of the new antimitotic drug MDL 27048 to the colchicine site of tubulin: equilibrium studies. Biochemistry 1992; 31:11125-11132.

41. Panda D, Singh J P, Wilson L. Suppression of microtubule dynamics by LY290181. J Biol Chem 1997; 272:7681-7687.
42. Andreu J M, Gorbunoff M J, Medrano F J, Rossi M, Timasheff S N. Mechanism of colchicine binding to tubulin. Tolerance of substituents in ring C' of biphenyl analogues. Biochemistry 1991; 30:3777-3786.
43. Aneja R, Lopus M, Zhou J, Vangapandu S N, Ghaleb A, Yao J, Nettles J H, Zhou B, Gupta M, Panda D, Chandra R, Joshi H C. Rational design of a microtubule targeting antibreast cancer drug, EM015. Cancer Res. (in press)

Having hereby disclosed the subject matter of the present invention, it should be apparent that many modifications, substitutions, and variations of the present invention are possible in light thereof. It is to be understood that the present invention can be practiced other than as specifically described. Such modifications, substitutions and variations are intended to be within the scope of the present application.

What is claimed:

1. A method of treating lung cancer comprising administering an effective amount of ((S)-6,7-dimethoxy-3-((R)-4-methoxy-6-methyl-9-bromo-5,6,7,8-tetrahydro-[1,3]dioxolo[4,5-g]isoquinolin-5-yl)isobenzofuran-1(3H)-one) or pharmaceutically acceptable salts thereof to a patient in need of treatment thereof.

2. The method of claim 1, wherein ((S)-6,7-dimethoxy-3-((R)-4-methoxy-6-methyl-9-bromo-5,6,7,8-tetrahydro-[1,3]dioxolo[4,5-g]isoquinolin-5-yl)isobenzofuran-1(3H)-one) or pharmaceutically acceptable salts thereof are administered orally.

3. The method of claim 1, wherein ((S)-6,7-dimethoxy-3-((R)-4-methoxy-6-methyl-9-bromo-5,6,7,8-tetrahydro-[1,3]dioxolo[4,5-g]isoquinolin-5-yl)isobenzofuran-1(3H)-one) or pharmaceutically acceptable salts thereof is administered in combination with at least one other anticancer agent.

4. The method of claim 3, wherein the other anticancer agent is selected from busulfan, cis-platin, mitomycin C, and carboplatin.

5. The method of claim 3, wherein the other anticancer agent is selected from colchicine, vinblastine, paclitaxel, and docetaxel.

6. The method of claim 3, wherein the other anticancer agent is selected from doxorubicin and etoposide.

* * * * *